US006291510B1

(12) United States Patent
Hamilton et al.

(10) Patent No.: US 6,291,510 B1
(45) Date of Patent: *Sep. 18, 2001

(54) SMALL MOLECULE INHIBITORS OF ROTAMASE ENZYME ACTIVITY

(75) Inventors: Gregory S. Hamilton, Catonsville; Joseph P. Steiner, Hampstead, both of MD (US)

(73) Assignee: GPI NIL Holdings, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/073,962

(22) Filed: May 7, 1998

Related U.S. Application Data

(63) Continuation-in-part of application No. 08/693,003, filed on Aug. 6, 1996, which is a continuation of application No. 08/479,436, filed on Jun. 7, 1995, now Pat. No. 5,614,547.

(51) Int. Cl.$^7$ .................................................. A61K 31/401
(52) U.S. Cl. ............................................................ 514/423
(58) Field of Search .............................................. 514/423

(56) References Cited

U.S. PATENT DOCUMENTS

| | | |
|---|---|---|
| 5,192,773 | 3/1993 | Armistead et al. . |
| 5,330,993 | 7/1994 | Armistead et al. . |
| 5,385,918 | 1/1995 | Connell et al. . |
| 5,614,547 | 3/1997 | Hamilton et al. . |
| 5,696,135 | 12/1997 | Steiner et al. . |
| 5,721,256 | 2/1998 | Hamilton et al. . |
| 5,786,378 | 7/1998 | Hamilton et al. . |
| 5,795,908 | 8/1998 | Hamilton et al. . |
| 5,798,355 | 8/1998 | Steiner et al. . |
| 5,801,187 | 9/1998 | Li et al. . |
| 5,801,197 | 9/1998 | Steiner et al. . |
| 6,037,370 | 3/2000 | Armistead . |

FOREIGN PATENT DOCUMENTS

WO 96/41609   12/1996   (WO) .

OTHER PUBLICATIONS

Hauske, James R. et al., "Design and Synthesis of Novel FKBP Inhibitors," *J. Med. Chem.*, 1992, 35, pp. 4284–4296.
Holt, Dennis A. et al., "Structure–Activity Studies of Non-macrocyclic Rapamycin Derivatives," *Bioorganic & Medical Chemistry Letters*, 1993, vol. 3, No. 10, pp. 1977–1980.
Yamashita, Dennis S. et al. "Design Synthesis and Evaluuation of Dual Domain FKBP Ligands," *Bioorganic & Medicinal Chemistry Letters*, 1994, vol. 4, No. 2 pp. 325–328.
Teague, Simon J. et al. "Synthesis and Study of a Non Macrocyclic FK506 Derivative," *Bioorganic & Medical Chemistry Letters*, 1994, vol. 4, No. 13, pp. 1581–1584.
Luengo, Juan I. et al. "Synthesis and Structure–Activity Relationships of Macrocyclic FKBP Ligands," *Bioorganic & Medicinal Chemistry Letters*, 1994, vol. 4, No. 2, pp. 321–324.
Holt, Dennis A. et al. "Structure–Activity Studies of Synthetic FKBP Ligands as Peptidyl–Prolyl Isomerase Inhibitors," *Bioorganic & Medicinal Chemistry Letters*, 1994, vol. 4, No. 2, pp. 315–320.
Teague, Simon J. et al. "The Affinity of the Excised Binding Domain of FK–506 for the Immunophilin FKBP12," *Bioorganic & Medicinal Chemistry Letters*, 1993, vol. 3, No. 10, pp. 1947–1950.
Caffrey, Moya V. et al. "Synthesis and Evaluation of Dual Domain Macrocyclic FKBP12 Ligands," *Bioorganic & Medicinal Chemistry Letters*, 1994, vol. 4, No. 21, pp. 2507–2510.
Birkenshaw, Timothy N. et al. "Synthetic FKBP12 Ligands. Design and Synthesis of Pyranose Replacements," *Bioorganic & Medicinal Chemistry Letters*, 1994, vol. 4, No. 21, pp. 2501–2506.
Holt, Dennis A. et al. "Design, Synthesis, and Kinetic Evaluation of High–Affinity FKBP Ligands and the X–Ray Crystal Structures of Their Complexes with FKBP12," *J. Am. Chem. Soc.*, 1993, 115, pp. 9925–9938.
Wang, Gary T. et al. "Synthesis and FKBP Binding of Small Molecule Mimics of the Tricarbonyl Region of FK506," *Bioorganic & Medicinal Chemistry Letters*, 1994, vol. 4, No. 9, pp. 1161–1166.
Snyder, Solomon H. and Sabatini David M., "Immunophilins and the Nervous System," *Nature Medicine*, 1995, vol. 1, No. 1, pp. 32–37.
Stocks, Michael J. et al. "The Contribution to Binding of the Pyranoside Substitutents in the Excised Binding Domain of FK–506," *Bioorganic & Medicinal Chemistry Letters*, 1994, vol. 4, No. 12, pp. 1457–1460.

*Primary Examiner*—Robert Gerstl
(74) *Attorney, Agent, or Firm*—Gary M. Nath; Todd L. Juneau; Joshua L. Goldberg

(57) ABSTRACT

This invention relates to neurotrophic compounds having an affinity for FKBP-type immunophilins, their preparation and use as inhibitors of the enzyme activity associated with immunophilin proteins, and particularly inhibitors of peptidyl-prolyl isomerase or rotamase enzyme activity.

4 Claims, No Drawings

SMALL MOLECULE INHIBITORS OF ROTAMASE ENZYME ACTIVITY

RELATED APPLICATIONS

This is a continuation-in-part application of U.S. patent application Ser. No. 08/693,003 filed Aug. 6, 1996, which is a continuation of U.S. patent application Ser. No. 08/479,436 filed Jun. 7, 1995 now U.S. Pat. No. 5,618,547.

BACKGROUND OF THE INVENTION

1. Field of the Invention

This invention relates to neurotrophic compounds having an affinity for FKBP-type immunophilins, their preparation and use as inhibitors of the enzyme activity associated with immunophilin proteins, and particularly inhibitors of peptidyl-prolyl isomerase or rotamase enzyme activity.

2. Description of the Prior Art

The term immunophilin refers to a number of proteins that serve as receptors for the principal immunosuppressant drugs, cyclosporin A (CsA), FK506, and rapamycin. Known classes of immunophilins are Cyclophilins, and FK506 binding proteins, such as FKBP. Cyclosporin A binds to cyclophilin while FK506 and rapamycin bind to FKBP. These immunophilin-drug complexes interface with a variety of intracellular signal transduction systems, especially in the immune system and the nervous system.

Immunophilins are known to have peptidyl-prolyl isomerase (PPIase) or rotamase enzyme activity. It has been determined that rotamase activity has a role in the catalyzation of the interconversion of the cis and trans isomer of immunophilin proteins.

Immunophilins were originally discovered and studied in immune tissue. It was initially postulated by those skilled in the art that inhibition of the immunophilins rotamase activity leads to the inhibition of T-cell proliferation, thereby causing the immunosuppressive action exhibited by immunosuppressive drugs such as cyclosporin A, FK506, and rapamycin. Further study has shown that the inhibition of rotamase activity, in and of itself, is not sufficient for immunosuppressant activity. Schreiber et al., *Science*, 1990 vol. 250 pp. 556–559. It has been shown that the immunophilin-drug complexes interact with ternary protein targets as their mode of action. Schreiber et al., *Cell*, 1991, vol. 66, pp. 807–815. In the case of FKBP-FK506 and FKBP-CsA, the drug-immunophilin complexes bind to the enzyme calcineurin, inhibitory T-cell receptor signalling leading to T-cell proliferation. Similarly, the complex of rapamycin and FKBP interacts with the RAFT1/FRAP protein and inhibits signalling from the IL-2 receptor.

Immunophilins have been found to be present at high concentrations in the central nervous system. Immunophilins are enriched 10–50 times more in the central nervous system than in the immune system. Within neural tissues, immunophilins appear to influence neuronal process extension, nitric oxide synthesis, and neurotransmitter release.

It has been found that picomolar concentrations of an immunosuppressant such as FK506 a nd rapamycin stimulate neurite out growth in PC12 cells and sensory nervous, namely dorsal root ganglion cells (DRGs). Lyons et al., *Proc. of Natl. Acad. Sci.*, 1994 vol. 91, pp. 3191–3195. In whole animal experiments, FK506 has been shown to stimulate nerve regeneration following facial nerve injury and results in functional recovery in animals with sciatic nerve lesions.

Surprisingly, it has been found that drugs with a high affinity for FKBP are potent rotarnase inhibitors causing a neurotrophic effect. Lyons et al. These findings suggest the use of immunosuppressants in treating various peripheral neuropathies and enhancing neuronal regrowth in the central nervous system (CNS). Studies have demonstrated that neurodegenerative disorders such as Alzheimer's disease, Parkinson's disease, and amyotrophic lateral sclerosis (ALS) may occur due to the loss, or decreased availability, of a neurotrophic substance specific for a particular population of neurons affected in the disorder.

Several neurotrophic factors effecting specific neuronal populations in the central nervous system have been identified. For example, it has been hypothesized that Alzheimer's disease results from a decrease or loss of nerve growth factor (NGF). It has thus been proposed to treat Alzheimer's patients with exogenous nerve growth factor or other neurotrophic proteins such as brain derived nerve factor (BDNF), glial derived nerve factor, ciliary neurotrophic factor, and neurotropin-3 to increase the survival of degenerating neuronal populations.

Clinical application of these proteins in various neurological disease states is hampered by difficulties in the delivery and bioavailability of large proteins to nervous system targets. By contrast, immunosuppressant drugs with neurotrophic activity are relatively small and display excellent bioavailability and specificity. However, when administered chronically, immunosuppressants exhibit a number of potentially serious side effects including nephrotoxicity, such as impairment of glomerular filtration and irreversible interstitial fibrosis (Kopp et al., 1991, *J. Am. Soc. Nephrol.* 1:162); neurological deficits, such as involuntary tremors, or non-specific cerebral angina such as non-localized headaches (De Groen et al., 1987, *N. Engl. J. Med.* 317:861); and vascular hypertension with complications resulting therefrom (Kahan et al., 1989 *N. Engl. J. Med.* 321:1725).

In order to prevent the side effects associated with use of the immunosuppressant compounds, the present invention provides non-immunosuppressive compounds containing small molecule FKBP rotamase inhibitors for promoting neuronal growth and regeneration in various neuropathological situations where neuronal repair can be facilitated including peripheral nerve damage by physical injury or disease state such as diabetes, physical damage to the central nervous system (spinal cord and brain) brain damage associated with stroke, and for the treatment of neurological disorders relating to neurodegeneration, including Parkinson's disease, Alzheimer's disease, and amyotrophic lateral sclerosis.

SUMMARY OF THE INVENTION

The present invention relates to a novel class of neurotrophic compounds having an affinity for FKBP-type immunophilins. Once bound to this protein the neurotrophic compounds are potent inhibitors of the enzyme activity associated with immunophilin proteins and particularly rotamase enzyme activity, thereby stimulating neuronal regeneration and outgrowth. A key feature of the compounds of the present invention is that they do not exert any significant immunosuppressive activity in addition to their neurotrophic activity.

The present invention further relates to a non-immunosuppressive neurotrophic N-glyoxyl prolyl ester compound or a non-immunosuppressive neurotrophic N-glyoxyl prolyl amide compound, excluding the derivative compounds of Examples 25–63 as embodied herein.

A preferred embodiment of this invention is a neurotrophic compound of the formula:

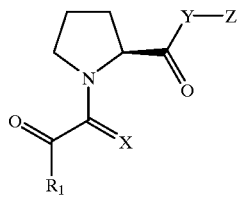

where

R$_1$ is selected from the group consisting of a C$_1$–C$_9$ straight or branched chain alkyl or alkenyl group optionally substituted with C$_3$–C$_8$ cycloalkyl, C$_3$ or C$_5$ cycloalkyl, C$_5$–C$_7$ cycloalkenyl, Ar$_1$, where said alkyl, alkenyl, cycloalkyl or cycloalkenyl groups may be optionally substituted with C$_1$–C$_4$ alkyl, C$_1$–C$_4$ alkenyl, or hydroxy, where Ar$_1$ is selected from the group consisting of 1-napthyl, 2-napthyl, 2-indolyl, 3-indolyl, 2-furyl, 3-furyl, 2-thiazolyl, 2-thienyl, 3-thienyl, 2-,3-, 4-pyridyl, and phenyl, having one to three substituents which are independently selected from the group consisting of hydrogen, halo, hydroxyl, nitro, trifluoromethyl, C$_1$–C$_6$ straight or branched alkyl or alkenyl, C$_1$–C$_4$ alkoxy or C$_1$–C$_4$ alkenyloxy, phenoxy, benzyloxy, and amino;

X is selected from the group consisting of oxygen, sulfur, methylene (CH$_2$), or H$_2$;

Y is selected from the group consisting of oxygen or NR$_2$, where R$_2$ is hydrogen or C$_1$–C$_6$ alkyl; and Z is selected from the group consisting of C$_2$–C$_6$ straight or branched chain alkyl or alkenyl, wherein the alkyl chain is substituted in one or more positions with Ar$_1$ as defined above, C$_3$–C$_8$ cycloalkyl, cycloalkyl connected by a C$_1$–C$_6$ straight or unbranched alkyl or alkenyl chain, and Ar$_2$ where Ar$_2$ is selected from the group consisting of 2-indolyl, 3-indolyl, 2-furyl, 3-furyl, 2-thiazolyl, 2-thienyl, 3-thienyl, 2-, 3-, or 4-pyridyl, and phenyl, having one to three substituents which are independently selected from the group consisting of hydrogen, halo, hydroxyl, nitro, trifluoromethyl, C$_1$–C$_6$ straight or branched alkyl or alkenyl, C$_1$–C$_4$ alkoxy or C$_1$–C$_4$ alkenyloxy, phenoxy, benzyloxy, and amino;

Z may also be the fragment:

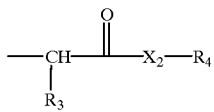

where

R$_3$ is selected from the group consisting of straight or branched alkyl C$_1$–C$_8$ optionally substituted with C$_3$–C$_8$ cycloalkyl, or Ar$_1$ as defined above, and unsubstituted Ar$_1$;

X$_2$ is O or NR$_5$, where R$_5$ is selected from the group consisting of hydrogen, C$_1$–C$_6$ straight or branched alkyl and alkenyl;

R$_4$ is selected from the group consisting of phenyl, benzyl, C$_1$–C$_5$ straight or branched alkyl or alkenyl, and C$_1$–C$_5$ straight or branched alkyl or alkenyl substituted with phenyl; or pharmaceutically acceptable salts or hydrates thereof;

provided that where Y is NR$_2$, X is selected from the group consisting of oxygen, sulfur, or methylene (CH$_2$); and excluding the N-glyoxyl prolyl ester derivative compounds of Examples 25–49 and 51–61.

Another preferred embodiment of this invention is a neurotrophic compound of the formula:

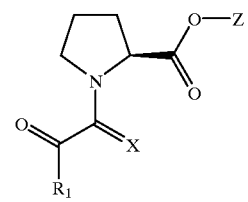

where

R$_1$ is a C$_1$–C$_9$ straight or branched chain alkyl or alkenyl group optionally substituted with C$_5$–C$_7$ cycloalkyl, C$_3$ or C$_5$ cycloalkyl, C$_5$–C$_7$ cycloalkenyl, or Ar$_1$, where said alkyl, alkenyl, cycloalkyl or cycloalkenyl groups may be optionally substituted with C$_1$–C$_4$ alkyl, C$_1$–C$_4$ alkenyl, or hydroxy, and where Ar$_1$ is selected from the group consisting of 1-napthyl, 2-napthyl, 2-indolyl, 3-indolyl, 2-furyl, 3-furyl, 2-thiazolyl, 2-thienyl, 3-thienyl, 2-, 3-, or 4-pyridyl, or phenyl, having one to three substituents which are independently selected from the group consisting of hydrogen, halo, hydroxyl, nitro, trifluoromethyl, C$_1$–C$_6$ straight or branched alkyl or alkenyl, C$_1$–C$_4$ alkoxy or C$_1$–C$_4$ alkenyloxy, phenoxy, benzyloxy, and amino;

X is oxygen;

Z is a C$_2$–C$_6$ straight or branched chain alkyl or alkenyl, wherein the alkyl chain is substituted in one or more positions with Ar$_1$ as defined above, C$_3$–C$_8$ cycloalkyl, cycloalkyl connected by a C$_1$–C$_6$ straight or unbranched alkyl or alkenyl chain, or Ar$_2$ where Ar2 is selected from the group consisting of 2-indolyl, 3-indolyl, 2-furyl, 3-furyl, 2-thiazolyl, 2-thienyl, 3-thienyl, 2-, 3-, or 4-pyridyl, or phenyl, having one to three substituents which are independently selected from the group consisting of hydrogen, halo, hydroxyl, nitro, trifluoromethyl, C$_1$–C$_6$ straight or branched alkyl or alkenyl, C$_1$–C$_4$ alkoxy or C$_1$–C$_4$ alkenyloxy, phenoxy, benzyloxy, and amino; or pharmaceutically acceptable salts or hydrates thereof;

provided that where Y is NR$_2$, X is selected from the group consisting of oxygen, sulfur, or methylene (CH$_2$); and excluding the N-glyoxyl prolyl ester derivative compounds of Examples 25–49 and 51–61.

Another preferred embodiment of this invention is a neurotrophic compound of the formula:

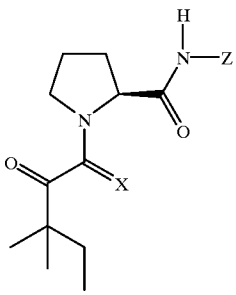

where
Z is the fragment:

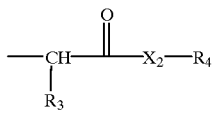

where
R₃ is selected from the group consisting of straight or branched alkyl $C_1$–$C_8$ optionally substituted with $C_3$–$C_8$ cycloalkyl, or $Ar_1$ as defined above, and unsubstituted $Ar_1$;

$X_2$ is O or $NR_5$, where $R_5$ is selected from the group consisting of hydrogen, $C_1$–$C_6$ straight or branched alkyl and alkenyl;

$R_4$ is selected from the group consisting of phenyl, benzyl, $C_1$–$C_5$ straight or branched alkyl or alkenyl, and $C_1$–$C_5$ straight or branched alkyl or alkenyl substituted with phenyl; or pharmaceutically acceptable salts or hydrates thereof; and provided that where Y is $NR_2$, X is selected from the group consisting of oxygen, sulfur, or methylene ($CH_2$).

Another preferred embodiment of the present invention is a method for treating a neurological disorder in an animal comprising administering a therapeutically effective amount of a non-immunosuppressive neurotrophic N-glyoxyl prolyl ester compound or a non-immunosuppressive neurotrophic N-glyoxyl prolyl amide compound.

Another preferred embodiment of the invention is a method of promoting neuronal regeneration and growth in mammals, comprising administering to a mammal an effective amount of a non-immunosuppressive neurotrophic N-glyoxyl prolyl ester compound or a non-immunosuppressive neurotrophic N-glyoxyl prolyl amide compound.

Yet another preferred embodiment of the invention is a method of preventing neurodegeneration in an animal comprising administering to an animal an effective amount of a non-immunosuppressive neurotrophic N-glyoxyl prolyl ester compound or a non-immunosuppressive neurotrophic N-glyoxyl prolyl amide compound.

Particularly preferred neurotrophic N-glyoxyl prolyl ester compounds according to the above formula are selected from the group consisting of:
3-(2,5-dimethoxyphenyl)-1-propyl (2S)-1-(3,3-dimethyl-1,2-dioxopentyl)-2-pyrrolidinecarboxylate,
3-(2,5-dimethoxyphenyl)-1-prop-2-(E)-enyl (2S)-1-(3,3-dimethyl-1,2-dioxopentyl)-2-pyrrolidinecarboxylate,
2-(3,4,5-trimethoxyphenyl)-1-ethyl (2S)-1-(3,3-dimethyl-1,2-dioxopentyl)-2-pyrrolidinecarboxylate,
3-(3-Pyridyl)-1-propyl (2S)-1-(3,3-dimethyl-1,2-dioxopentyl)-2-pyrrolidinecarboxylate,
3-(2-Pyridyl)-1-propyl (2S)-1-(3,3-dimethyl-1,2-dioxopentyl)-2-pyrrolidinecarboxylate,
3-(4-Pyridyl)-1-propyl (2S)-1-(3,3-dimethyl-1,2-dioxopentyl)-2-pyrrolidinecarboxylate,
3-phenyl-1-propyl (2S)-1-(2-tert-butyl-1,2-dioxoethyl)-2-pyrrolidinecarboxylate,
3-phenyl-1-propyl (2S)-1-(2-cyclohexylethyl-1,2-dioxoethyl)-2-pyrrolidinecarboxylate,
3-(3-pyridyl)-1-propyl (2S)-1-(2-cyclohexylethyl-1,2-dioxoethyl)-2-pyrrolidinecarboxylate,
3-(3-pyridyl)-1-propyl (2S)-1-(2-tert-butyl-1,2-dioxoethyl)-2-pyrrolidinecarboxylate,
3,3-diphenyl-1-propyl (2S)-1-(3,3-dimethyl-1,2-dioxopentyl)-2-pyrrolidinecarboxylate,
3-(3-pyridyl)-1-propyl (2S)-1-(2-cyclohexyl-1,2-dioxoethyl)-2-pyrrolidinecarboxylate,
3-(3-pyridyl)-1-propyl (2S)-N-(2-[2-thienyl]glyoxyl)-2-pyrrolidinecarboxylate,
3,3-Diphenyl-1-propyl (2S)-1-cyclohexylglyoxyl-2-pyrrolidinecarboxylate, and
3,3-Diphenyl-1-propyl (2S)-1-(2-thienyl)glyoxyl-2-pyrrolidinecarboxylate.

DETAILED DESCRIPTION OF THE INVENTION

The novel neurotrophic compounds of this invention are relatively small molecules in relation to other known compounds which bind to FKBP-type immunophilins, such as rapamycin, FK506, and cyclosporin.

The neurotrophic compounds of this invention have an affinity for the FK506 binding proteins such as FKBP-12. When the neurotrophic compounds of the invention are bound to the FKBP, they have been found to unexpectedly inhibit the prolyl-peptidyl cis-trans isomerase activity, or rotamase activity of the binding protein.

The compounds of this invention exist as stereoisomeric forms, either enantiomers or diastereoisomers. The stereochemistry at position 1 (Formula 1) is R or S, with S preferred. Included within the scope of the invention are the enantiomers, the racemic form, and diastereoisomeric mixtures. Enantiomers as well as diastereoisomers can be separated by methods known to those skilled in the art.

It is known that immunophilins such as FKBP preferentially recognize peptide substrates containing Xaa-Pro-Yaa motifs, where Xaa and Yaa are lipophilic amino acid residues. Schreiber et al. 1990 *J. Org. Chem.* 55, 4984–4986; Harrison and Stein, 1990 *Biochemistry*, 29, 3813–3816. Thus modified prolyl peptidomimetic compounds bearing lipophilic substituents should bind with high affinity to the hydrophobic core of the FKBP active site and inhibit its rotamase activity.

Preferred compounds of the invention include:
3-(4,5-dichlorophenyl)-1-propyl (2S)-1-(3,3-dimethyl-1,2-dioxopentyl)-2-pyrrolidinecarboxylate,
3-(4,5-methylenedioxyphenyl)-1-propyl (2S)-1-(3,3-dimethyl-1,2-dioxopentyl)-2-pyrrolidinecarboxylate,
3-cyclohexyl-1-propyl (2S)-1-(3,3-dimethyl-1,2-dioxopentyl)-2-pyrrolidinecarboxylate,
3-cyclohexyl-1-prop-2-(E)-enyl (2S)-1-(3,3-dimethyl-1,2-dioxopentyl)-2-pyrrolidinecarboxylate,
(1R)-1,3-diphenyl-1-prop-2-(E)-enyl (2S)-1-(3,3-dimethyl-1,2-dioxopentyl)-2-pyrrolidinecarboxylate, (1R)-1-cyclohexyl-3-phenyl-1-propyl (2S)-1-(3,3-dimethyl-1,2-dioxopentyl)-2-pyrrolidinecarboxylate, (1R)-1-cyclohexyl-3-phenyl-1-prop-2-(E)-enyl (2S)-1-(3,3-dimethyl-1,2-dioxopentyl)-2-pyrrolidinecarboxylate, (1R)-1-(4,5-dichlorophenyl)-3-phenyl-1-propyl (2S)-1-(3,3-dimethyl-1,2-dioxopentyl)-2-pyrrolidinecarboxylate, 3-phenyl-1-propyl (2S)-1-(1,2-dioxo-2-cyclohexyl)ethyl-2-pyrrolidinecarboxylate, 3-phenyl-1-propyl (2S)-1-(1,2-dioxo-4-cyclohexyl)butyl-2-pyrrolidinecarboxylate, 3-phenyl-1-propyl ($^2$S)-1-(1,2-dioxo-2-[2-furanyl])ethyl-2-pyrrolidinecarboxylate, 3-phenyl-1-propyl (2S)-1-(1,2-dioxo-2-[2-thienyl)ethyl-2-pyrrolidinecarboxylate, 3-phenyl-1-propyl (2S)-1-(1,2-dioxo-2-[2-thiazolyl])ethyl-2-pyrrolidinecarboxylate, 3-phenyl-1-propyl (2S)-1-(1,2-dioxo-2-phenyl)ethyl-2-pyrrolidinecarboxylate, 1,7-diphenyl-4-heptyl (2S)-1-(3,3-dimethyl-1,2-dioxopentyl)-2-pyrrolidinecarboxylate, 3-Phenyl-1-propyl (2S)-1-(3,3-dimethyl-1,2-dioxo-4-hydroxybutyl)-2-pyrrolidinecarboxylate, 3-phenyl-1-propyl (2S)-1-(3,3-dimethyl-1,2-dioxopentyl)-2-pyrrolidinecarboxamide, 1-[1-(3,3-dimethyl-1,2-dioxopentyl)-L-proline-L-phenylalanine ethyl ester, 1-[1-(3,3-dimethyl-1,2-dioxopentyl)-L-proline]-L-leucine ethyl ester, 1-[1-(3,3-dimethyl-1,2-dioxopentyl)-L-proline]-L-phenylglycine ethyl ester, 1-[1-(3,3-dimethyl-1,2-dioxopentyl)-L-proline]-L-phenylalanine phenyl ester, 1-[1-(3,3-dimethyl-1,2-dioxopentyl)-L-proline]-L-phenylalanine benzyl ester, 1-[1-(3,3-dimethyl-1,2-dioxopentyl)-L-proline]-L-isoleucine ethyl ester, 3-(2,5-dimethoxyphenyl)-1-propyl (2S)-1-(3,3-dimethyl-1,2-dioxopentyl)-2-pyrrolidinecarboxylate, 3-(2,5-dimethoxyphenyl)-1-prop-2-(E)-enyl (2S)-1-(3,3-dimethyl-1,2-dioxopentyl)-2-pyrrolidinecarboxylate, 2-(3,4,5-trimethoxyphenyl)-1-ethyl (2S)-1-(3,3-dimethyl-1,2-dioxopentyl)-2-pyrrolidinecarboxylate, 3-(3-Pyridyl)-1-propyl (2S)-1-(3,3-dimethyl-1,2-dioxopentyl)-2-pyrrolidinecarboxylate, 3-(2-Pyridyl)-1-propyl (2S)-1-(3,3-dimethyl-1,2-dioxopentyl)-2 -pyrrolidinecarboxylate, 3-(4-Pyridyl)-1-propyl (2S)-1-(3,3-dimethyl-1,2-dioxopentyl)-2-pyrrolidinecarboxylate, 3-phenyl-1-propyl (2S)-1-(2-tert-butyl-1,2-dioxaethyl)-2-pyrrolidinecarboxylate, 3-phenyl-1-propyl (2S)-1-(2-cyclohexylethyl-1,2-dioxoethyl)-2-pyrrolidinecarboxylate, 3-(3-pyridyl)-1-propyl (2S)-1-(2-cyclohexylethyl-1,2-dioxoethyl)-2-pyrrolidinecarboxylate, 3-(3-pyridyl)-1-propyl (2S)-1-(2-tert-butyl-1,2-dioxoethyl)-2-pyrrolidinecarboxylate, 3,3-diphenyl-1-propyl (2S)-1-(3,3-dimethyl-1,2-dioxopentyl)-2-pyrrolidinecarboxylate, 3-(3-pyridyl)-1-propyl (2S)-1-(2-cyclohexyl-1,2-dioxoethyl)-2-pyrrolidinecarboxylate, 3-(3-pyridyl)-1-propyl (2S)-N-(2-[2-thienyl]glyoxyl)-2-pyrrolidinecarboxylate, 3,3-Diphenyl-1-propyl (2S)-1-cyclohexylglyoxyl-2-pyrrolidinecarboxylate, and 3,3-Diphenyl-1-propyl (2S)-1-(2-thienyl)glyoxyl-2-pyrrolidinecarboxylate.

The compounds of the present invention may be useful in a free base form, in the form of base salts where possible, and in the form of addition salts, as well as in the free acid form. All these forms are within the scope of the invention. In practice, use of the salt form amounts to use of the base form.

Pharmaceutically acceptable salts within the scope of the invention include those derived from mineral acids, such as hydrochloric acid and sulfuric acid, and those derived from organic acids, such as ethanesulfonic acid, benzenesulfonic acid, p-toluenesulfonic acid, and the like, giving the corresponding hydrochloride, sulfonate, ethanesulfonate, benzenesulfonate, p-toluenesulfonate, and the like, of those derived from the neutral compound.

Examples of suitable inorganic bases for the formation of salts of compounds of the invention include the hydroxides, carbonates, and bicarbonates of ammonia; sodium; lithium; potassium; calcium; magnesium; aluminum; zinc; and the like.

Salts may also be formed with suitable organic bases. Organic bases suitable for the formation of pharmaceutically acceptable base addition salts with compounds of the present invention include those that are non-toxic and strong enough to form such salts. These organic bases and the use thereof are readily understood by those skilled in the art. For purposes of illustration, the class of such organic bases may include mono-, di-, and trialkylamines, such as methylamine, dimethylamine, and triethylamine; mono-, di- or trihydroxyalkylamines, such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl) aminoethane; and the like. See, for example, "Pharmaceutical Salts," *J. Pharm. Sci.*, 66:1, 1–19 (1977).

The acid addition salts of the basic compounds may be prepared either by dissolving the compound of the present invention in an aqueous or an aqueous alcohol solution or other suitable solvent containing the appropriate acid or base, and isolating the salt by evaporating the solution. Alternatively, the free base of the compound of the present invention may be reacted with an acid, as well as reacting the compound of the present invention having an acid group thereon with a base, such that the reactions are in an organic solvent, in which case the salt separates directly or can be obtained by concentrating the solution.

The neurotrophic compounds of this invention can be periodically administered to a patient undergoing treatment for neurological disorders or for other reasons in which it is desirable to stimulate neuronal regeneration and growth, such as in various peripheral neuropathic and neurological disorders relating to neurodegeneration. The compounds of this invention can also be administered to mammals other than humans for treatment of various mammalian neurological disorders.

The novel compounds of the present invention are potent inhibitors of rotamase activity and possess an excellent degree of neurotrophic activity. This activity is useful in the stimulation of damaged neurons, the promotion of neuronal regeneration, the prevention of neurodegeneration, and in the treatment of several neurological disorders known to be associated with neuronal degeneration and peripheral neuropathies. The neurological disorders that may be treated include but are not limited to: trigeminal neuralgia, glossopharyngeal neuralgia, Bell's Palsy, myasthenia gravis, muscular dystrophy, amyotrophic lateral sclerosis, progressive muscular atrophy, progressive bulbar inherited muscular atrophy, herniated, ruptured or prolapsed invertabrae disk syndromes, cervical spondylosis, plexus disorders, thoracic outlet destruction syndromes, peripheral neuropathic such as those caused by lead, dapsone, ticks, prophyria, or Gullain-Barré syndrome, Alzheimer's disease, and Parkinson's disease.

For these purposes, the composition of the invention may be administered orally, parenterally, by inhalation spray, topically, rectally, nasally, bucally, vaginally, intraventricularly, via an implanted reservoir in dosage formulations containing conventional non-toxic pharmaceutically-acceptable carriers, or by any other convenient dosage form. The term parenteral as used herein includes subcutaneous, intravenous, intramuscular, intraperitoneal, intrathecal, intraventricular, intrasternal, and intracranial injection or infusion techniques.

When administered parenterally, the composition will normally be in a unit dosage, sterile injectable form (solution, suspension or emulsion) which is preferably isotonic with the blood of the recipient with a pharmaceutically acceptable carrier. Examples of such sterile injectable forms are sterile injectable aqueous or oleaginous suspensions. These suspensions may be formulated according to techniques known in the art using suitable dispersing or wetting agents and suspending agents. The sterile injectable forms may also be sterile injectable solutions or suspensions in non-toxic parenterally-acceptable diluents or solvents, for example, as solutions in 1,3-butanediol. Among the acceptable vehicles and solvents that may be employed are water, saline, Ringer's solution, dextrose solution, isotonic sodium chloride solution, and Hanks' solution. In addition, sterile, fixed oils are conventionally employed as solvents or suspending mediums. For this purpose, any bland fixed oil may be employed including synthetic mono- or di-glycerides, corn, cottonseed, peanut, and sesame oil. Fatty acids such as ethyl oleate, isopropyl myristate, and oleic acid and its glyceride derivatives, including olive oil and castor oil, especially in their polyoxyethylated versions, are useful in the preparation of injectables. These oil solutions or suspensions may also contain long-chain alcohol diluents or dispersants.

Sterile saline is a preferred carrier, and the compounds are often sufficiently water soluble to be made up as a solution for all foreseeable needs. The carrier may contain minor amounts of additives, such as substances that enhance solubility, isotonicity, and chemical stability, e.g, anti-oxidants, buffers and preservatives.

Formulations suitable for nasal or buccal administration (such as self-propelling powder dispensing formulations) may comprise about 0.1% to about 5% w/w, for example 1% w/w of active ingredient. The formulations for human medical use of the present invention comprise an active ingredient in association with a pharmaceutically acceptable carrier therefore and optionally other therapeutic ingredient(s).

When administered orally, the composition will usually be formulated into unit dosage forms such as tablets, cachets, powder, granules, beads, chewable lozenges, capsules, liquids, aqueous suspensions or solutions, or similar dosage forms, using conventional equipment and techniques known in the art. Such formulations typically include a solid, semisolid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, and the like.

The composition of the invention is preferably administered as a capsule or tablet containing a single or divided dose of the inhibitor. Preferably, the composition is administered as a sterile solution, suspension, or emulsion, in a single or divided dose. Tablets may contain carriers such as lactose and corn starch, and/or lubricating agents such as magnesium stearate. Capsules may contain diluents including lactose and dried corn starch.

A tablet may be made by compressing or molding the active ingredient optionally with one or more accessory ingredients. Compressed tablets may be prepared by compressing, in a suitable machine, the active ingredient in a free-flowing form such as a powder or granuLes, optionally mixed with a binder, lubricant, inert diluent, surface active, or dispersing agent. Molded tablets may be made by molding in a suitable machine, a mixture of the powdered active ingredient and a suitable carrier moistened with an inert liquid diluent.

The compounds of this invention may also be administered rectally in the form of suppositories. These compositions can be prepared by mixing the drug with a suitable nonirritating excipient which is solid at room temperature, but liquid at rectal temperature, and, therefore, will melt in the rectum to release the drug. Such materials include cocoa butter, beeswax, and polyethylene glycols Compositions and methods of the invention also may utilize controlled release technology. Thus, for example, the inventive compounds may be incorporated into a hydrophobic polymer matrix for controlled release over a period of days. The composition of the invention may then be molded into a solid implant suitable for providing efficacious concentrations of the compound of the present invention over a prolonged period of time without the need for frequent re-dosing. Such controlled release films are well known to the art. Particularly preferred are transdermal delivery systems. Other examples of polymers commonly employed for this purpose that may be used in the present invention include nondegradable ethylene-vinyl acetate copolymer an degradable lactic acid-glycolic acid copolymers which may be used externally or internally. Certain hydrogels such as poly(hydroxyethylmethacrylate) or poly(vinylalcohol) also may be useful, but for shorter release cycles than the other polymer release systems, such as those mentioned above.

The compounds of the present invention are used in the composition in amounts that are therapeutically effective. Said compositions may be sterilized and/or contain adjuvants, such as preserving, stabilizing, welling, or emulsifying agents, solution promoters, salts for regulating the osmotic pressure, and/or buffers. In addition, they may also contain other therapeutically valuable substances. Said compositions are prepared according to conventional mixing, granulating, or coating methods, and contain about 0.1 to 75%, preferably about 1 to 50%, of the active ingredient.

To be effective therapeutically as central nervous system targets, the compounds of the present invention should readily penetrate the blood-brain barrier when peripherally administered. Compounds which cannot penetrate the blood-brain barrier can be effectively administered by an intraventricular route or other appropriate delivery system suitable for administration to the brain.

Doses of the compounds preferably include pharmaceutical dosage units comprising an efficacious quantity of active compound. By an efficacious quantity is meant a quantity sufficient to derive the beneficial effects through administration of one or more of the pharmaceutical dosage units. Preferably, the dose is sufficient to reduce the effects of neurodegenerative diseases.

For medical use, the amount required of the active ingredient to achieve a therapeutic effect will vary with the particular compound, the route of administration, the mammal under treatment, and the particular disorder or disease being treated. A suitable systematic dose of a compound of the present invention or a pharmacologically acceptable salt thereof for a mammal suffering from, or likely to suffer from, any of condition as described hereinbefore is in the range of about 0.1 mg/kg to about 100 mg/kg of the active ingredient compound, the most preferred dosage being about 1 to about 10 mg/kg.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

It is understood that the ordinarily skilled physician or veterinarian will readily determine and prescribe the effective amount of the compound for prophylactic or therapeutic treatment of the condition for which treatment is administered. In so proceeding, the physician or veterinarian could employ an intravenous bolus followed by an intravenous infusion and repeated administrations, parenterally or orally, as considered appropriate. While it is possible for an active ingredient to be administered alone, it is preferable to present it as a formulation.

When preparing dosage form incorporating the compositions of the invention, the compounds may also be blended with conventional excipients such as binders, including gelatin, pregelatinized starch, and the like; lubricants, such as hydrogenated vegetable oil, stearic acid, and the like; diluents, such as lactose, mannose, and sucrose; disintegrants, such as carboxymethylcellulose and sodium starch glycolate; suspending agents, such as povidone, polyvinyl alcohol, and the like; absorbants, such as silicon dioxide; preservatives, such as methylparaben, propylparaben, and sodium benzoate; surfactants, such as sodium lauryl sulfate, polysorbate 80, and the like; colorants such as F.D.& C. dyes and lakes; flavorants; and sweeteners.

The compounds can be administered with other neurotrophic agents such as neurotrophic growth factor (NGF), glial derived growth factor, brain derived growth factor, ciliary neurotrophic factor, and neurotropin-3. The dosage level of other neurotrophic drugs will depend upon the factors previously stated and the neurotrophic effectiveness of the drug combination.

$K_i$ Test Procedure

Inhibition of the peptidyl-prolyl isomerase (rotamase) activity of the inventive compounds can be evaluated by known methods described in the literature (Harding, M. W. et al. *Nature* 341: 758–760 (1989); Holt et al. *J. Am. Chem. Soc.* 115: 9923–9938). These values are obtained as apparent $K_i$'s and are presented for some of Examples 1–30 in Table I. The cis-trans isomerization of an alanine-proline bond in a model substrate, N-succinyl-Ala-Ala-Pro-Phe-p-nitroanilide, is monitored spectrophotometrically in a chymotrypsin-coupled assay, which releases para-nitroanilide from the trans form of the substrate. The inhibition of this reaction caused by the addition of different concentrations of inhibitor is determined, and the data is analyzed as a change in first-order rate constant as a function of inhibitor concentration to yield the apparent $K_i$ values.

In a plastic cuvette are added 950 mL of ice cold assay buffer (25 mM HEPES, pH 7.8, 100 mM NaCl), 10 mL of FKBP (2.5 mM in 10 mM Tris-Cl pH 7.5, 100 mM NaCl, 1 mM dithiothreitol), 25 mL of chymotrypsin (50 mg/ml in 1 mM HCl) and 10 mL of test compound at various concentrations in dimethyl sulfoxide. The reaction is initiated by the addition of 5 mL of substrate (succinyl-Ala-Phe-Pro-Phe-para-nitroanilide, 5 mg/mL in 2.35 mM LiCl in trifluoroethanol).

The absorbance at 390 nm versus time is monitored for 90 sec using a spectrophotometer and the rate constants are determined from the absorbance versus time data files.

The data for these experiments is presented in Table I.

TABLE I

| FKBP ROTAMASE INHIBITION | |
|---|---|
| Example | $K_i$ nM |
| 4 | 42 |
| 5 | 125 |
| 6 | 200 |
| 7 | 65 |
| 8 | 2500 |
| 9 | 160 |
| 10 | 52 |
| 24 | 9000 |

In mammalian cells, FKBP-12 complexes with the inositol triphosphate receptor ($IP_3R$) and the ryanodine receptor (RyR). It is believed that the neurotrophic compounds of this invention disassociates FKBP-12 from these complexes causing the calcium channel to become "leaky" (Cameron et al., 1995). Calcium fluxes are involved in neurite extensions so that the $IP_3R$ receptor and the ryanodine receptor might be involved in the neurotrophic effects of drugs. Since the drugs bind to the same site as FKBP-12 as the $IP_3R$ receptor, one could assume that the drugs displace the channels from FKBP-12.

Chick Dorsal Root Ganglion

Cultures and Neurite Outgrowth

Dorsal root ganglia were dissected from chick embryos of ten day gestation. Whole ganglion explants were cultured on thin layer Matrigel-coated 12 well plates with Liebovitz L15 plus high glucose media supplemented with 2 mM glutamine and 10% fetal calf serum, and also containing 10 $\mu$M cytosine $\beta$-D arabinofuranoside (Ara C) at 37° C. in an environment containing 5% $CO_2$. Twenty-four hours later, the DRGs were treated with various concentrations of nerve growth factor, immunophilin ligands or combinations of NFG plus drugs. Forty-eight hours after drug treatment, the ganglia were visualized under phase contrast or Hoffman Modulation contrast with a Zeiss Axiovert inverted microscope. Photomicrographs of the explants were made, and neurite outgrowth was quantitated. Neurites longer than the DRG diameter were counted as positive, with total number of neurites quantitated per each experimental condition. Three to four DRGs are cultured per well, and each treatment was performed in duplicate.

The data for these experiments are presented in Table II.

TABLE II

| Neurite Outgrowth in Chick DRG | |
|---|---|
| Example | $ED_{50}(nM)$ |
| 4 | 53 |
| 5 | 105 |
| 6 | 149 |
| 7 | 190 |
| 8 | 850 |
| 9 | 75 |
| 10 | — |
| 24 | — |

The following examples are illustrative of preferred embodiments of the invention and are not to be construed as limiting the invention thereto. All polymer molecular weights are mean average molecular weights. All percentages are based on the percent by weight of the final delivery system or formulation prepared unless otherwise indicated and all totals equal 100% by weight.

EXAMPLES

The inventive compounds may be prepared by a variety of synthetic seqfuences that utilize established chemical transformations. The general pathway to the present compounds is described in Scheme 1. N-glyoxylproline derivatives may be prepared by reacting L-proline methyl ester with methyl oxalyl chloride as shown in Scheme I. The resulting oxamates may be reacted with a variety of carbon nucleophiles to obtain intermediates compounds. These intermediates are then reacted with a variety of alcohols, amides, or protected amino acid residues to obtain the propyl esters and amides of the invention

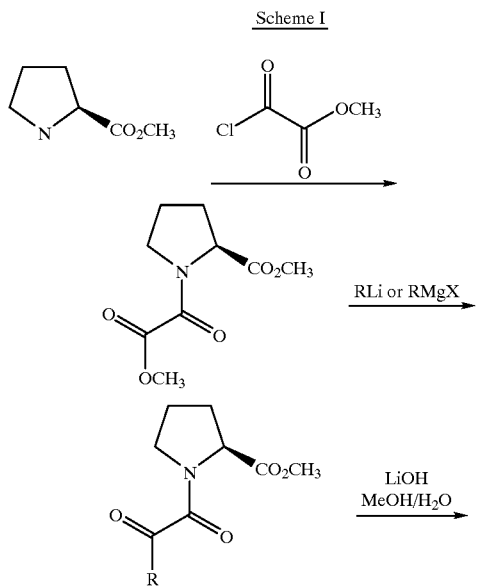

Scheme I

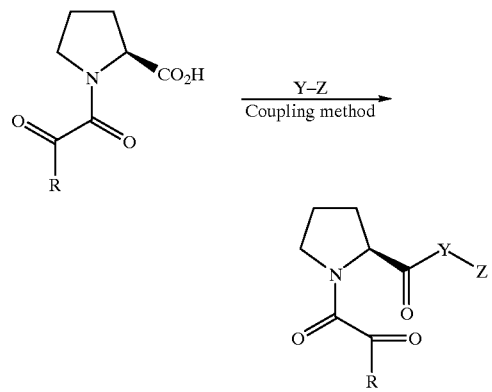

Scheme I

Example 1

Synthesis of methyl (2S)-1-(1,2-dioxo-2-methoxyethyl)-2-pyrrolidinecarboxylate.

A solution of L-proline methyl ester hydrochloride (3.08 g; 18.60 mmol) in dry methylene chloride was cooled to 0° C. and treated with triethylamine (3.92 g; 38.74 mmol; 2.1 eq). After stirring the formed slurry under a nitrogen atmosphere for 15 min, a solution of methyl oxalyl chloride (3.20 g; 26.12 mmol) in methylene chloride (45 ml) was added dropwise. The resulting mixture was stirred at 0° C. for 1.5 hr. After filtering to remove solids, the organic phase was washed with water, dried over $MgSO_4$ and concentrated. The crude residue was purified on a silica gel column, eluting with 50% ethyl acetate in hexane, to obtain 3.52 g (88%) of the product as a reddish oil. Mixture of cis-trans amide rotamers; data for trans rotamer given. $^1H$ NMR ($CDCl_3$): d 1.93 (dm, 2H); 2.17 (m, 2H); 3.62 (m, 2H); 3.71 (s, 3H); 3.79, 3.84 (s, 3H total); 4.86 (dd, 1H, J=8.4, 3.3).

Example 2

General procedure for the synthesis of pyrrolidinyl alkyl oxamates. Exemplified for methyl (2S)-1-(1,2-dioxo-3,3-dimethylpentyl)-2-pyrrolidinecarboxylate.

A solution of methyl (2S)-1-(1,2-dioxo-2-methoxyethyl)-2-pyrrolidinecarboxylate (2.35 g; 10.90 mmol) in 30 mL of tetrahydrofuran (THF) was cooled to −78° C. and treated with 14.2 mL of a 1.0 M solution of 1,1-dimethylpropylmagnesium chloride in THF. After stirring the resulting homogeneous mixture at −78° C. for three hours, the mixture was poured into saturated ammonium chloride (100 mL) and extracted into ethyl acetate. The organic phase was washed with water, dried, and concentrated, and the crude material obtained upon removal of the solvent was purified on a silica gel column, eluting with 25% ethyl acetate in hexane, to obtain 2.10 g (75%) of the oxamate as a colorless oil. $^1H$ NMR ($CDCl_3$): d 0.88 (t, 3H); 1.22, 1.26 (s, 3H each); 1.75 (dm, 2H); 1.87–2.10 (m, 3H); 2.23 (m, 1H); 3.54 (m, 2H); 3.76 (s, 3H); 4.52 (dm, 1H, J=8.4, 3.4).

Example 3

General procedure for the preparation of pyrrolidine carboxylic acids. Exemplified for (2S)-1-(1,2-dioxo-3,3-dimethylpentyl)-2-pyrrolidinecarboxylic acid.

A mixture of methyl (2S)-1-(1,2-dioxo-3,3-dimethylpentyl)-2-pyrrolidinecarboxylate (2.10 g; 8.23 mmol), 1 N LiOH (15 mL), and methanol (50 mL) was stirred at 0° C. for 30 min and at room temperature overnight. The mixture was acidified to pH 1 with 1 N HCl, diluted with water, and extracted into 100 mL of methylene chloride. The organic extract was washed with brine and concentrated to deliver 1.73 g (87%) of snow-white solid which did not require further purification. $^1$H NMR (CDCl$_3$): d 0.87 (t, 3H); 1.22, 1.25 (s, 3H each); 1.77 (dm, 2H); 2.02 (m, 2H); 2.17 (m, 1H); 2.25 (m, 1H); 3.53 (dd, 2H, J=10.4, 7.3); 4.55 (dd, 1H, J=8.6, 4.1).

Example 4

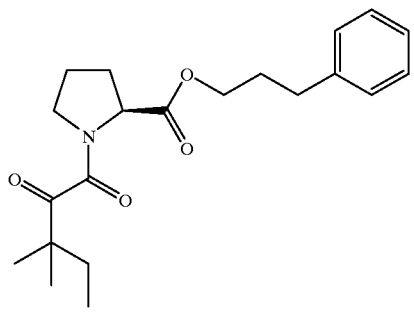

General procedure for the synthesis of prolyl esters. Exemplified for 3-phenyl-1-propyl (2S)-1-(3,3-dimethyl-1,2-dioxopentyl)-2-pyrrolidinecarboxylate. A mixture of (2S)-1-(1,2-dioxo-3,3-dimethylpentyl)-2-pyrrolidine-carboxylic acid (600 mg; 2.49 mmol), 3-phenyl-1-propanol (508 mg; 3.73 mmol), dicyclohexylcarbodiimide (822 mg; 3.98 mmol), camphorsulphonic acid (190 mg; 0.8 mmol) and 4-dimethylaminopyridine (100 mg; 0.8 mmol) in methylene chloride (20 mL) was stirred overnight under a nitrogen atmosphere. The reaction mixture was filtered through Celite to remove solids and concentrated in vacuo, and the crude material was purified on a flash column (25% ethyl acetate in hexare) to obtain 720 mg (80%) of the product as a colorless oil. $^1$H NMR (CDCl$_3$): d 0.84 (t, 3H); 1.19 (s, 3H); 1.23 (s, 3H); 1.70 (dm, 2H); 1.98 (m, 5H); 2.22 (m, 1H); 2.64 (m, 2H); 3.47 (m, 2H); 4.14 (m, 2H); 4.51 (d, 1H); 7.16 (m, 3H); 7.26 (m, 2H).

Example 5

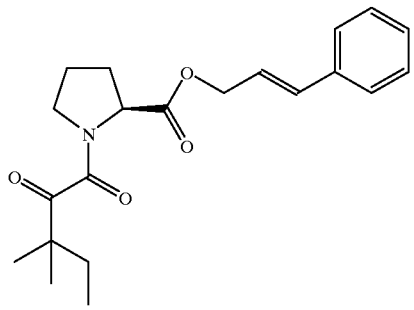

3-Phenyl-1-prop-2-(E)-enyl (2S)-1-(3,3-dimethyl-1,2-dioxopentyl)-2-pyrrolidinecarboxylate, 80%, $^1$H NMR (360 Mhz, CDCl$_3$): d 0.86 (t, 3H); 1.21 (s, 3H); 1.25 (s, 3H); 1.54–2.10 (m, 5H); 2.10–2.37 (m, 1H); 3.52–3.55 (m, 2H); 4.56 (dd, 1H, J=3.8, 8.9); 4.78–4.83 (m, 2H); 6.27 (m, 1H); 6.67 (dd, 1H, J=15.9); 7.13–7.50 (m, 5H). This compound was prepared by the method of Example 3 from (2S)-1-(1,2-dioxo-3,3-dimethylpentyl)-2-pyrrolidine-carboxylic acid.

Example 6

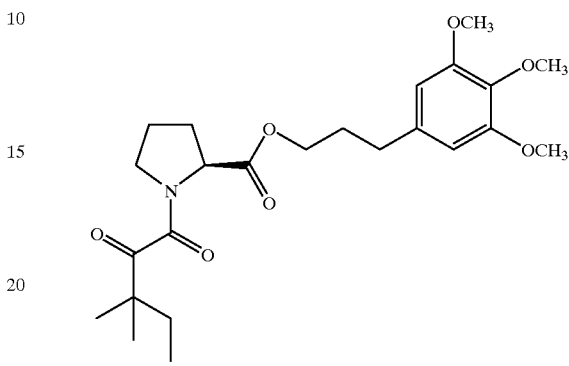

3-(3,4,5-Trimethoxyphenyl)-1-propyl (2S)-1-(3,3-dimethyl-1,2-dioxopentyl)-2-pyrrolidinecarboxylate, 61%, $^1$H NMR (CDCl$_3$): d 0.84 (t, 3H); 1.15 (s, 3H); 1.24 (s, 3H); 1.71 (dm, 2H); 1.98 (m, 5H); 2.24 (m, 1H); 2.63 (m, 2H); 3.51 (t, 2H); 3.79 (s, 3H); 3.83 (s, 3H); 4.14 (m, 2H); 4.52 (m, 1H); 6.36 (s, 2H). This compound was prepared by the method of Example 3 from (2S)-1-(1,2-dioxo-3,3-dimethylpentyl)-2-pyrrolidine-carboxylic acid.

Example 7

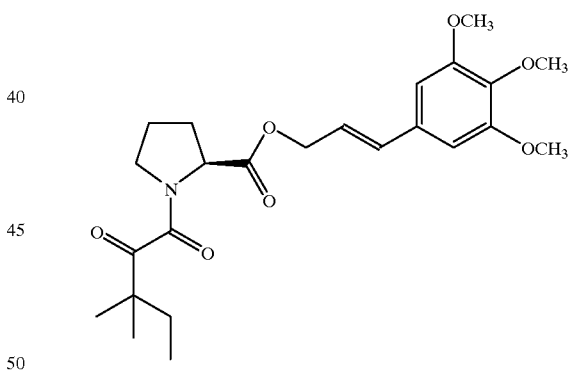

3-(3,4,5-Trimethoxyphenyl)-1-prop-2-(E)-enyl (2S)-1-(3,3-dimethyl-1,2-dioxopentyl)-2-pyrrolidinecarboxylate, 66%, $^1$H NMR (CDCl$_3$): d 0.85 (t, 3H); 1.22 (s, 3H); 1.25 (s, 3H); 1.50–2.11 (m, 5H); 2.11–2.40 (m, 1H); 3.55 (m, 2H); 3.85 (s, 3H); 3.88 (s, 6H); 4.56 (dd, 1H); 4.81 (m, 2H); 6.22 (m, 1H); 6.58 (d, 1H, J=16); 6.63 (s, 2H). This compound was prepared by the method of Example 3 from (2S)-1-(1,2-dioxo-3,3-dimethylpentyl)-2-pyrrolidine-carboxylic acid.

Example 8

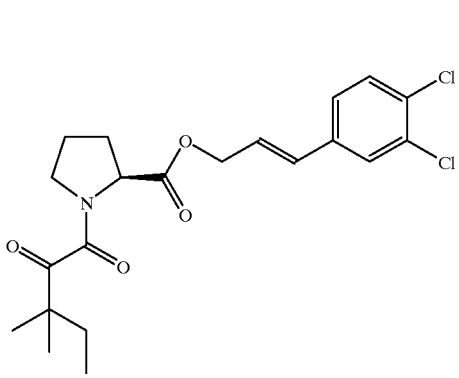

3-,4,5-Dichlorophenyl)-1-prop-2-(E)-enyl (2S)-1-(3,3-dimethyl-1,2-dioxopentyl)-2-pyrrolidinecarboxylate, 70%, $^1$H NMR (CDCl$_3$): d 0.85 (t, 3H); 1.21 (s, 3H); 1.25 (s, 3H); 1.51–1.87 (m, 2H); 1.87–2.39 (m, 4H); 3.51–3.57 (m, 2H); 4.50–4.61 (dd, 1H, J=3.4, 8.6); 4.80 (d, 2H, J=6.0); 6.20–6.34 (m, 1H); 6.50–6.66 (d, 1H, J=16); 7.13–7.24 (dd, 1H, J=1.8, 8.3); 7.39 (d, 1H, J=8.3); 7.47 (s, 1H). This compound was prepared by the method of Example 3 from (2S)-1-(1,2-dioxo-3,3-dimethylpentyl)-2-pyrrolidine-carboxylic acid.

Example 9

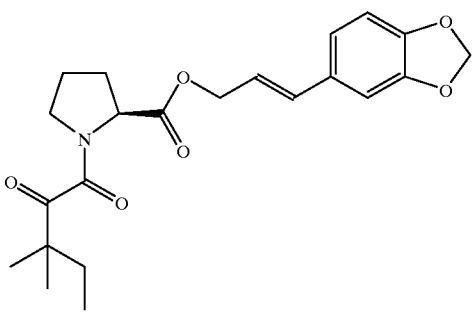

3-(4,5-Methylenedioxyphenyl)-1-prop-2-(E)-enyl (2S)-1-(3,3-dimethyl-1,2-dioxopentyl)- 2-pyrrolidinecarboxylate, 82%, $^1$H NMR (360 MHz, CDCl$_3$): d 0.86 (t,3H); 1.22 (s, 3H); 1.25 (s, 3H); 1.60–2.10 (m, 5H); 3.36–3.79 (m, 2H); 4.53 (dd, 1H, J=3.8, 8.6); 4.61–4.89 (m, 2H); 5.96 (s, 2H); 6.10 (m, 1H); 6.57 (dd, 1H, J=6.2, 15.8); 6.75 (d, 1H, J=8.0); 6.83 (dd, 1H, J=1.3, 8.0); 6.93 (s, 1H). This compound was prepared by the method of Example 3 from (2S)-1-(1,2-dioxo-3,3-dimethylpentyl)-2-pyrrolidine-carboxylic acid.

Example 10

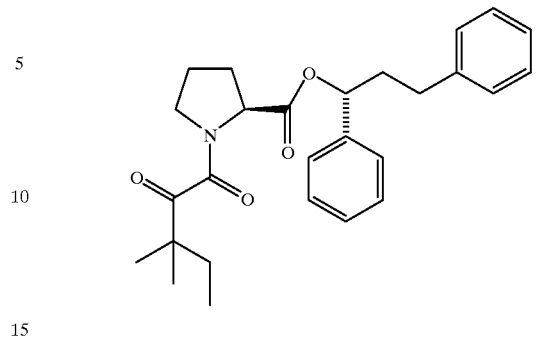

(1R)-1,3-Diphenyl-1-propyl (2S)-1-(3,3-dimethyl-1,2-dioxopentyl)-2-pyrrolidinecarboxylate, 90%, $^1$H NMR (360 MHz, CDCl$_3$): d 0.85 (t, 3H); 1.20 (s, 3H); 1.23 (s, 3H); 1.49–2.39 (m, 7H); 2.46–2.86 (m, 2H); 3.25–3.80 (m, 2H); 4.42–4.82 (m, 1H); 5.82 (td, 1H, J=1.8, 6.7); 7.05–7.21 (m, 3H); 7.21–7.46 (m, 7H). This compound was prepared by the method of Example 3 from (2S)-1-(1,2-dioxo-3,3-dimethylpentyl)-2-pyrrolidine-carboxylic acid.

Example 11

The requisite substituted alcohols may be prepared by a number of methods known to those skilled in the art of organic synthesis. As described in Scheme II, substituted benzaldehydes may be homologated to phenyl propanols by reaction with methyl (triphenylphosphoranylidene)— acetate to provide a variety of trans-cinnamates; these latter may be reduced to the saturated alcohols by reaction with excess lithium aluminum hydride, or sequentially by reduction of the double bond by catalytic hydrogenation and reduction of the saturated ester by appropriate reducing agents. Alternatively, the trans-cinnamates may be reduced to (E)-allylic alcohols by the use of diisobutylaluminum hydride.

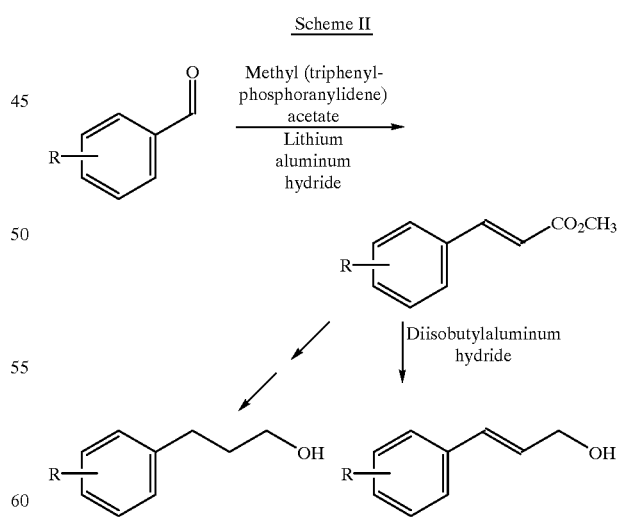

Scheme II

Longer chain alcohols may be prepared by homologation of benzylic and higher aldehydes. Alternatively, these aldehydes may be prepared by conversion of the corresponding phenylacetic and higher acids, and phenethyl and higher alcohols.

Example 12

General procedure for the synthesis of acrylic esters, exemplified for methyl (3,3,5-trimethoxy)-trans-cinnamate.

A solution of 3,4,5-trimethoxybenzaldehyde (5.0 g; 25.48 mmol) and methyl (triphenyl-phosphoranylidene)acetate (10.0 g; 29.91 mmol) in tetrahydrofuran (250 mL) was refluxed overnight. After cooling, the reaction mixture was diluted with 200 mL of ethyl acetate and washed with 2×200 mL of water, dried, and concentrated in vacuo. The crude residue was chromatographed on a silica gel column, eluting with 25% ethyl acetate in hexane, to obtain 5.63 g (88%) of the cinnamate as a white crystalline solid, $^1$H NMR (300 Mhz; $CDCl_3$): d 3.78 (s, 3H); 3.85 (s, 6H); 6.32 (d, 1H, J=16); 6.72 (s, 2H); 7.59 (d, 1H, J=16).

Example 13

Methyl (4,5-dichloro)-trans-cinnamate, 80%, $^1$H NMR (300 Mhz; $CDCl_3$): d 3.79 (s, 3H); 6.40 (d, 1H, J=16.8); 7.32 (dd, 1H, J=1.5, 8.1); 7.44 (d, 1H, J=8.1); 7.56 (d, 1H, J=16); 7.58 (s, 1H). This compound was prepared by the method of Example 11 from 3,4,5-trimethoxybenzaldehyde.

Example 14

Methyl (4,5-methylenedioxy)-trans-cinnamate, 74%, $^1$H NMR (360 Mhz; $CDCl_3$): d 3.79 (s, 3H); 6.01 (s, 2H); 6.26 (d, 1H, J=16); 6.81 (d, 1H, J=7.9); 7.00 (d, 1H, J=8.2); 7.03 (s, 1H); 7.60 (d, 1H, J=16). This compound was prepared by the method of Example 11 from 3,4,5-trimethoxybenzaldehyde.

Example 15

Methyl (2-cyclohexyl)-(E)-acrylate, 80%, $^1$H NMR (360 Mhz; $CDCl_3$): d 1.12–1.43 (m, 5H); 1.52–1.87 (m, 5H); 2.12 (m, 1H); 3.71 (s, 3H); 5.77 (dd, 1H, J=1.2, 15.8); 6.92 (dd, 1H, J=6.8, 15.8). This compound was prepared by the method of Example 11 from 3,4,5-trimethoxybenzaldehyde.

Example 16

General procedure for the synthesis of saturated alcohols from acrylic esters. Exemplified for (3,4,5-trimethoxy) phenylpropanol.

A solution of methyl (3,3,5-trimethoxy)-trans-cinnamate (1.81 g; 7.17 mmol) in tetrahydrofuran (30 mL) was added in a dropwise manner to a solution of lithium aluminum hydride (14 mmol) in THF (35 mL), with stirring and under an argon atmosphere. After the addition was complete, the mixture was heated to 75° C. for 4 hours. After cooling, it was quenched by the careful addition of 15 mL of 2N NaOH followed by 50 mL of water. The resulting mixture was filtered through Celite to remove solids, and the filter cake was washed with ethyl acetate. The combined organic fractions were washed with water, dried, concentrated in vacuo, and purified on a silica gel column, eluting with ethyl acetate to obtain 0.86 g (53%) of the alcohol as a clear oil, $^1$H NMR (300 Mhz; $CDCl_3$): d 1.23 (br, 1H); 1.87 (m, 2H); 2.61 (t, 2H, J=7.1); 3.66 (t, 2H); 3.80 (s, 3H); 3.83 (s, 6H); 6.40 (s, 2H).

Example 17

General procedure for the synthesis of trans-allylic alcohols from acrylic esters. Exemplified for (3,4,5-trimethoxy) phenylprop-2-(E)-enol.

A solution of methyl (3,3,5-trimethoxy)-trans-cinnamate (1.35 g; 5.35 mmol) in toluene (25 mL) was cooled to −10° C. and treated with a solution of diisobutylaluminum hydride in toluene (11.25 mL of a 1.0 M solution; 11.25 mmol). The reaction mixture was stirred for 3 hrs at 0° C. and then quenched with 3 mL of methanol followed by 1 N HCl until the pH was 1. The reaction mixture was extracted into ethyl acetate and the organic phase was washed with water, dried and concentrated. Purification on a silica gel column eluting with 25% ethyl acetate in hexane furnished 0.96 g (80%) of a thick oil, 1H NMR (360 Mhz; $CDCl_3$): d 3.85 (s, 3H); 3.87 (s, 6H); 4.32 (d, 2H, J=5.6); 6.29 (dt, 1H, J=15.8, 5.7), 6.54 (d, 1H, J=15.8); 6.61 (s, 2H).

Example 18

(4,5-dichloro)phenylprop-2-(E)-enol, 89%, $^1$H NMR (360 Mhz; $CDCl_3$): d 1.55 (s, 1H); 4.34 (d, 2H, J=4.4); 6.36 (dt, 1H, J=15.9, 5.3); 6.54 (d, 1H, J=15.9); 7.20 (dd, 1H, J=8.3, 1.7); 7.38 (d, 1H, J=8.3); 7.45 (d, 1H, J=1.6). This compound was prepared by the method of Example 16 from (3,4,5-tri-methoxy)-trans-cinnamate.

Example 19

(4,5-methylenedioxy)phenylprop-2-(E)-enol, 80%, $^1$H NMR (360 Mhz; $CDCl_3$): d 1.59 (br, 1H); 4.29 (br, 2H); 5 5.96 (s, 2H); 6.20 (dt, 1H, J=15.8, 5.9); 6.52 (d, 1H, J=15.8); 6.76 (d, 1H, J=8.0); 6.82 (dd, 1H, J=8.0, 1.2); 6.93 (d, 1H, J=1.2). This compound was prepared by the method of Example 16 from (3,4,5-tri-methoxy)-trans-cinnamate.

Example 20

Phenylprop-2-(E)-enol, 85g, $^1$H NMR (360 Mhz; $CDCl_3$); d 1.72 (br, 1H); 4.31 (d, 2H, J=5.7); 6.36 (dt, 1H, J=15.9, 5.7); 6.61 (d, 1H, J=15.9); 7.02–7.55 (m, 5H). This compound was prepared by the method of Example 16 from (3,4,5-tri-methoxy)-trans-cinnamate.

Example 21

Alcohols containing a substituent at the 1-position of the side chain may be conveniently prepared by addition of appropriate nucleophiles to aldehydes, as described in Scheme 20I. In cases where optically active substituted alcohols are desired, the racemic alcohols may be oxidized to prochiral ketones and subjected to asymmetric reduction by one of several methods well known to those skilled in the art.

Scheme III

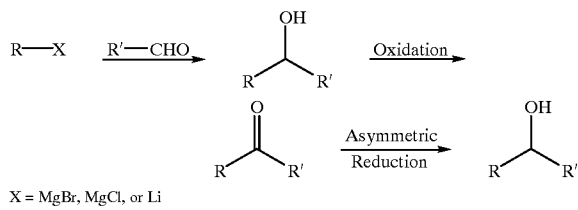

X = MgBr, MgCl, or Li

Example 22

General procedure for the preparation of 1-substituted alkanols, exemplified for the synthesis of 1,3-diphenylpropanol.

A solution of 2-(bromoethyl)benzene (17.45 g; 94.3 mmol) in 50 mL of dry diethyl ether was added dropwise, under a nitrogen atmosphere, to a stirred slurry of magnesium turnings (2.50 g; 102.8 mmol) in 50 mL of ether. The mixture was initially heated with a heat gun until reflux had become self-sustaining. After the addition was complete, the mixture was heated externally for 30 min to maintain reflux. A solution of 10.01 g (94.3 mmol) of benzaldehyde in 20 mL of ether was then added dropwise, and reflux was continued for 30 min. After cooling, the reaction mixture was poured into 150 um of saturated ammonium chloride and extracted into ethyl acetate. The crude material obtained upon removal of the solvent was purified on a flash column, eluting with 5% ethyl acetate/hexane to 20% ethyl acetate, to obtain 13.73 g (69%) of the alkanol as a light yellow oil, $^1$H NMR (360 Mhz; CDCl$_3$): d 1.93–2.30 (m, 3H); 2.70–2.90 (m, 2H); 4.72 (br, 1H); 7.19–7.27 (m, 3H); 7.27–7.36 (m, 3H); 7.36–7.47 (m, 4H).

Example 23

General procedure for conversion of racemic 1-substituted alkanols to optically active 1-substituted alkanols via prochiral ketones. Exemplified for (1R)-1,3-diphenyl-1-propanol.

A solution of racemic 1,3-diphenyl-1-propanol (1.26 g; 5.94 mmol) was dissolved in 10 mL of acetone, and Jones reagent was added until persistence of the orange color. After stirring for 30 min, the reaction was quenched by adding 2 mL of 2-propanol. The solvent was decanted away from the precipitated solids, which were washed with ethyl acetate. The combined organic fractions were washed with 2×20 mL of water, dried and concentrated. The crude product was filtered through a plug of silica gel, eluting with 25% ethyl acetate/hexane, to obtain 1.07 g (86%) of 1,3-diphenylpropanone as a white crystalline solid, $^1$H NMR (360 Mhz; CDCl$_3$): d 3.09 (t, 2H, J=8.1); 3.33 (t, 2H, J=8.1); 7.29 (m, 5H); 7.49 (m, 3H); 7.98 (m, 2H).

A solution of 1,3-diphenylpropanone (1.07 g; 5.09 mmol) in tetrahydrofuran (10 mL) was cooled to −23° C. and treated with an asymmetric reducing agent, (+)-B-chlorodiisopinocampheyl-borane (1.80 g; 5.60 mmol) in 20 mL THF, and the resulting solution was allowed to stand overnight at −23° C. After evaporating to dryness, the residue was treated with ether (65 mL) and diethanolamine (1.0 g) and stirred for 3 hrs. The mixture was then filtered to remove solids and concentrated, and the residue was purified using gradient elution (5% ethyl acetate/hexane to 10% ethyl acetate) on a silica gel column to obtain 660 mg (61%) of (IR)-1,3-diphenyl-1-propanol as a crystalline white solid, $^1$H NMR (360 Mhz; CDCl$_3$): d 1.95–2.15 (m, 3H); 2.59–2.78 (m, 2H); 4.65 (dd, 1H, J 5.4, 7.8); 7.14–7.35 (m, 10H).

Example 24

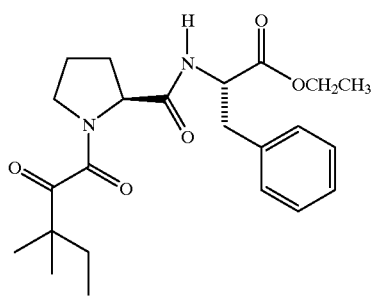

General procedure for the synthesis of prolyl dipeptides, exemplified for 1-[1-(3,3-dimethyl-1,2-dioxopentyl)-L-proline]-L-phenylalanine ethyl ester.

A mixture of (2S)-1-(1,2-dioxo-3,3-dimethylpentyl)-2-pyrrolidinecarboxylic acid (1.17 g; 4.85 mmol), L-phenylalanine ethyl ester hydrochloride (1.23 g; 5.33 mmol), dicyclohexylcarbo-diimide (1.10 g; 5.33 mmol) and 4-dimethylaminopyridine (60 mg (4.85 mmol) in methylene chloride (25 mL) was treated with triethylamine (1 mL; 726 mg; 7.17 mmol) and stirred overnight. The mixture was filtered through Celite to remove solids and concentrated, and the crude material from removal of the solvent was purified on a silica gel column eluting with 30% ethyl acetate/hexane to obtain 2.02 g of 1-[1-(3,3-dimethyl-1,2-dioxopentyl)-L-proline]-L-phenylalanine ethyl ester, 100%, $^1$H NMR (360 MHz, CDCl$_3$): d 0.87 (t, 3H); 1.16–1.28 (m, 9H); 1.58–1.91 (m, 5H); 2.33 (m, 1H); 3.07–3.20 (m, 2H); 3.38–3.41 (m, 2H); 4.11–4.18 (m, 4H); 4.55 (d, 1H, J=6.5); 4.78–4.80 (m, 1H); 7.15 (br d, 1H); 7.19 (m, 5H).

Example 25

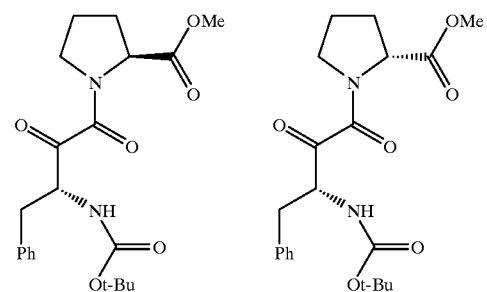

These compounds, which are named L-Proline, 1-[3[[(1,1-dimethylethoxy)carbonyl]amino]-1,2-dioxo-4-phenylbutyl]-, methyl ester, (R) and L-Proline, 1-[3[[(1,1-dimethylethoxy) carbonyl] amino]-1,2-dioxo-4-phenylbutyl]-, methyl ester, (S), are dislosed by Munoz et al., *Bioorg. Med. Chem.*, 1994, 2(10), 1085–90.

Example 26

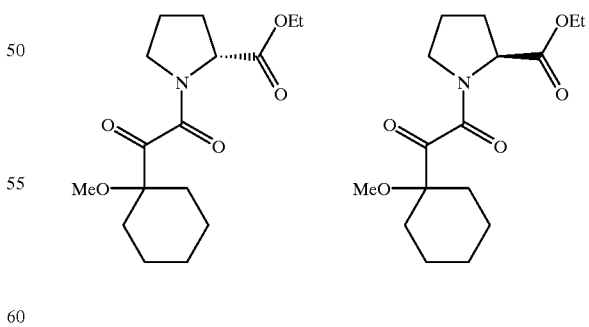

These compounds which are named L-Proline, 1-[(1-methoxycyclohexyl) oxoacetyl]-, ethyl ester, and D-Proline, 1-[(1-methoxycyclohexyl) oxoacetyl]-, ethyl ester, are disclosed by Holt et al., *Bioorg. Med. Chem. Lett.*, 1994, 4(2), 315–20.

Example 27

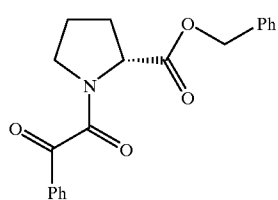

This compound, which is named L-Proline, 1-(oxophenylacetyl)-, phenylmethyl ester, is disclosed by Armistead et al., U.S. Pat. No. 5,192,773, which issued Mar. 9, 1993.

Example 28

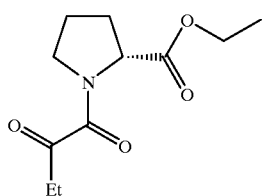

This compound, which is named L-Proline, 1-(1,2-dioxobutyl)-phenylmethyl ester, is disclosed by Armistead et al., U.S. Pat. No. 5,192,773, which issued Mar. 9, 1993.

Example 29

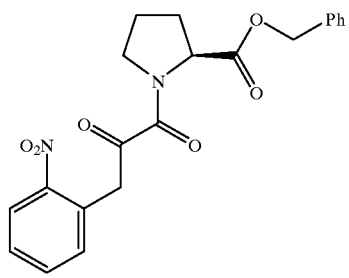

This compound, which is named L-Proline, 1-[3-(2-nitrophenyl)-1,2-dioxopropyl]-, phenylmethyl ester, is disclosed by Armistead et al., U.S. Pat. No. 5,192,773, which issued Mar. 9, 1993.

Example 30

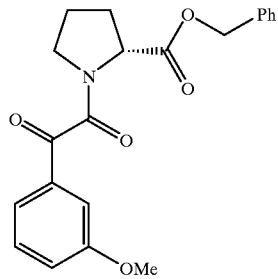

This compound, which is named L-Proline, 1-[(3-methoxyphenyl) oxoacetyl]-, phenylmethyl ester, is disclosed by Armistead et al., U.S. Pat. No. 5,192,773, which issued Mar. 9, 1993.

Example 31

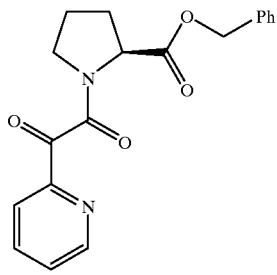

This compound, which is named L-Proline, 1-(oxo-2-pyridinylacetyl)-, phenylmethyl ester, is disclosed by Armistead et al., U.S. Pat. No. 5,192,773, which issued Mar. 9, 1993.

Example 32

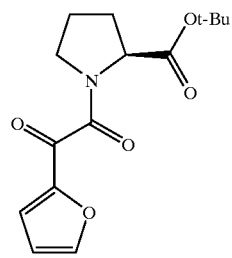

This compound, which is named L-Proline, 1-(2-furanyloxoacetyl)-, 1,1-dimethylethyl ester, is disclosed by Armistead et al., U.S. Pat. No. 5,192,773, which issued Mar. 9, 1993.

Example 33

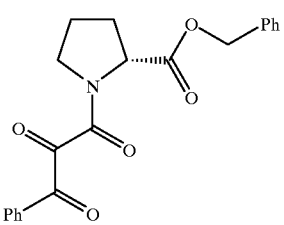

This compound, which is named L-Proline, 1-(1,2,3-trioxo-3-phenylpropyl)-phenylmethyl ester, is disclosed by Pattendan, G. and Tankard, M., *Tetrahedron Lett.*, 1993, 34(16), 2677–80.

Example 34

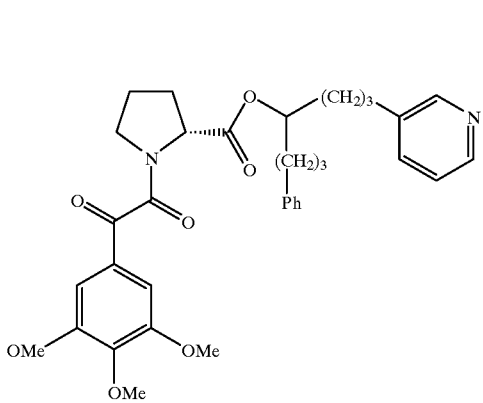

This compound, which is named L-Proline, 1-[oxo-(3,4,5-trimethoxyphenyl) acetyl]-1-(3-phenylpropyl)-4-(2-pyridinyl) butyl ester, is disclosed in Armistead, D., PCT Int. Appl. WO9219593 A1, which was published Nov. 12, 1992.

Example 35

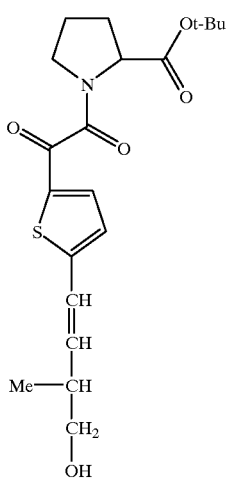

This compound, which is named L-Proline, 1-[[5-(4-hydroxy-3-methyl-1-butenyl)-2-thienyl] oxoacetyl]-, 1,1-dimethylethyl ester, is disclosed in Hauske et al., *J. Med. Chem.*, 1992, 35(23), 4284–96.

Example 36

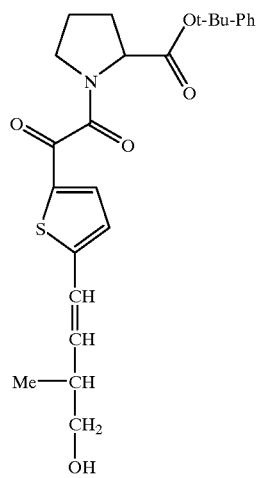

This compound, which is named L-Proline, 1-[[5-(4-hydroxy-3-methyl-1-butenyl)-2-thienyl] oxoacetyl]-, 1,1-dimethylethyl ester, is disclosed in Hauske et al., *J. Med. Chem.*, 1992, 35(23), 4284–96.

Example 37

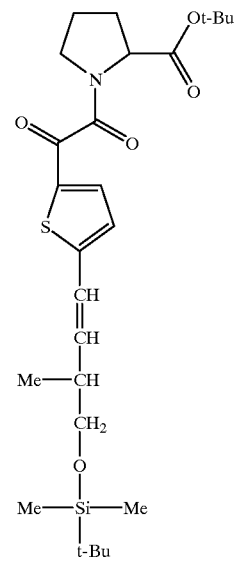

This compound, which is named L-Proline, 1-[[5-[4[[(1,1-dimethylethyl)dimethylsilyl]oxyl]-3-methyl-1-butenyl]-2-thienyl]oxoaacetyl]-, 1,1-dimethylethyl ester, [R-(E)], is disclosed in Hauske et al., *J. Med. Chem.*, 1992, 35(23), 4284–96.

Example 38

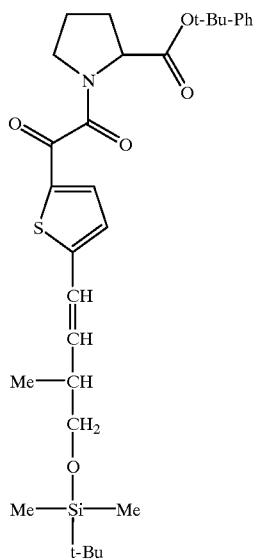

This compound, which is named L-Proline, 1-[[5-[4[[(1,1-dimethylethyl)dimethylsilyl]oxy]-3-methyl-1-butenyl]-2-thienyl]oxoacetyl]-, 1,1-dimethylethyl ester, [R-(E)], is disclosed in Hauske et al., *J. Med. Chem.*, 1992, 35(23), 4284–96.

Example 39

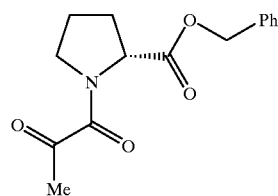

This compound, which is named L-Proline, 1-(1,2-dioxopropyl)-, phenylmethyl ester, is disclosed in Rinehart, K. and Lithgow-Bertelloni, A., PCT Int. Appl. WO9104985 A1, which was published Apr. 18, 1991.

Example 40

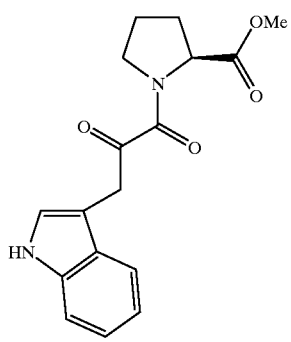

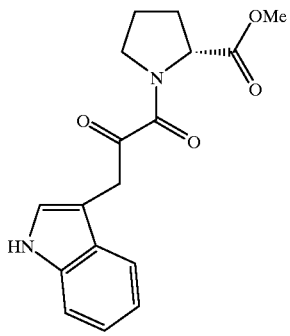

These compounds, which are named L-Proline, 1-[3-(1H-indol-3-yl)-1,2-dioxopropyl]-, methyl ester and D-Proline, 1-[3-(1H-indol-3-yl)-1,2-dioxopropyl]-, methyl ester, are disclosed in De Luca et al., U.S. Pat. No. 5,002,963, which issued Mar. 26, 1991.

Example 41

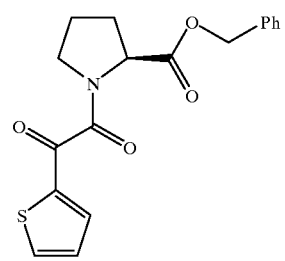

This compound, which is named L-Proline, 1-(oxo-2-thienylacetyl)-, phenylmethyl ester, is disclosed in Waldmann, H., *Liebigs Ann. Chem.*, 1991, (12), 1317–22.

Example 42

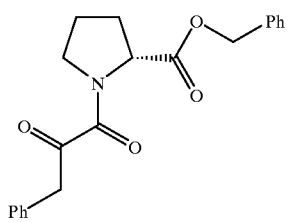

This compound, which is named L-Proline, 1-(1,2-dioxo-3-phenylpropyl)-, phenylmethyl ester, is disclosed in Waldmann, H., *Liebigs Ann. Chem.*, 1991, (12), 1317–22.

Example 43

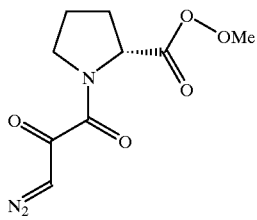

This compound, which is named L-Proline, 1-(3-diazo-1,2-dioxopropyl)-, methyl ester, is disclosed in Goodfellow et al., *Biochemistry*, 1989, 28(15), 6346–60.

Example 44

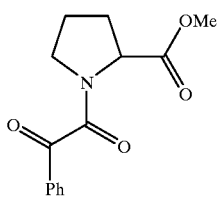

This compound, which is named L-Proline, 1-(oxophenylacetyl)-, methyl ester, is disclosed in Boulmedais et al., *Bull. Soc. Chim. Fr.*, 1989, (2), 185–91.

Example 45

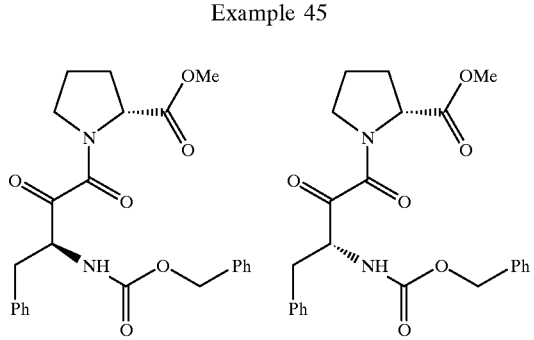

These compounds, which are named L-Proline, 1-[1,2-dioxo-4-phenyl-3-[[(phenylmethoxy)carbony]amino]butyl]-, methyl ester, (S) and L-Proline, 1-[1,2-dioxo-4-phenyl-3-([[(phenylmethoxy)carbonyl]amino]butyl]-, methyl ester, (R), are disclosed in Slee et al., *J. Am. Chem. Soc.*, 1995, 117(48), 11867–78.

Example 46

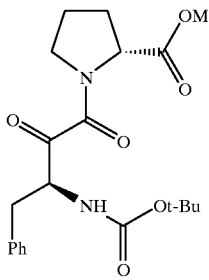 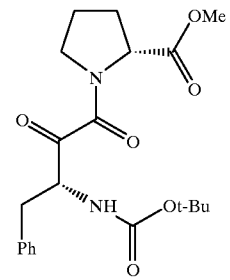

These compounds, which are named L-Proline, 1-[3-[[1,1-dimethylethoxy)carbonyl]amino]-1,2-dioxo-4-phenylbutyl]-, methyl ester, (S) and L-Proline, 1-[3-[[1,1-dimethylethoxy)carbonyl]amino]-1,2-dioxo-4-phenylbutyl]-, methyl ester, (R), are disclosed in Slee et al., *J. Am. Chem. Soc.*, 1995, 117(48), 11867–78.

Example 47

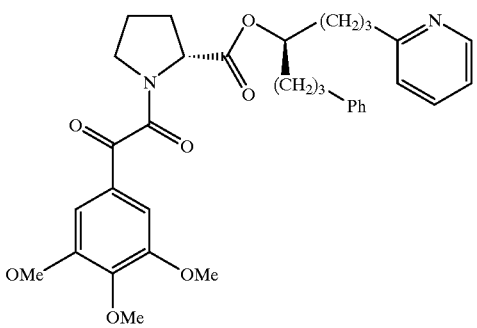

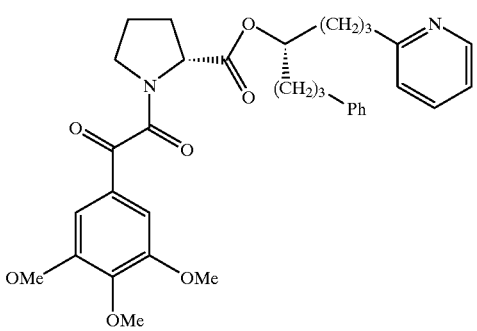

These compounds, which are named L-Proline, 1-oxo(3,4,5-trimethoxyphenyl)acetyl]-, 1-(3-phenylpropyl)-4-(2-pyridinyl) butyl ester, (S) and L-Proline, 1-[oxo(3,4,5-trimethoxyphenyl)acetyl]-, 1-(3-phenylpropyl)-4-(2-pyridinyl) butyl ester, (R), are disclosed in Armistead et al., Int. Appl. WO9407858 A1, which was published Apr. 14, 1994.

31
Example 48

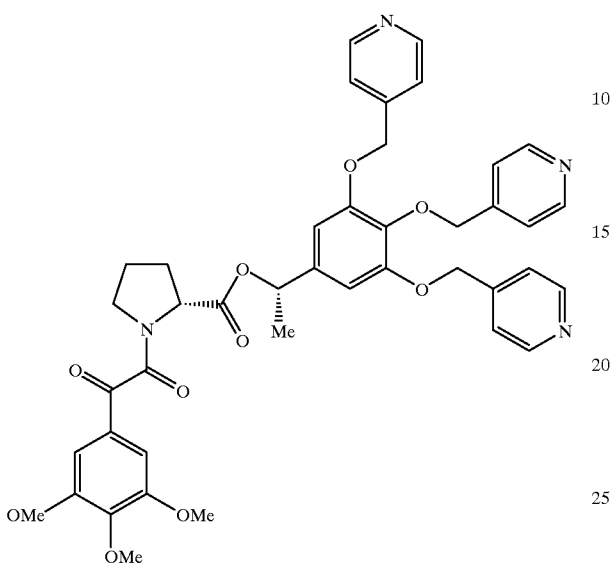

These compounds, which are named L-Proline, 1-[oxo(3,4,5-trimethoxyphenyl)acetyl]-, (1S)-1-[3,4,5-tris(4-pyridinylmethoxy)phenyl] ethyl ester and L-Proline, 1-[oxo(3,4,5-trimethoxyphenyl) acetyl]-, (1R)-1-[3,4,5-tris(4-pyridinylmethoxy)phenyl] ethyl ester, are disclosed in Armistead et al., Int. Appl. WO9407858 A1, which was published Apr. 14, 1994.

32
Example 49

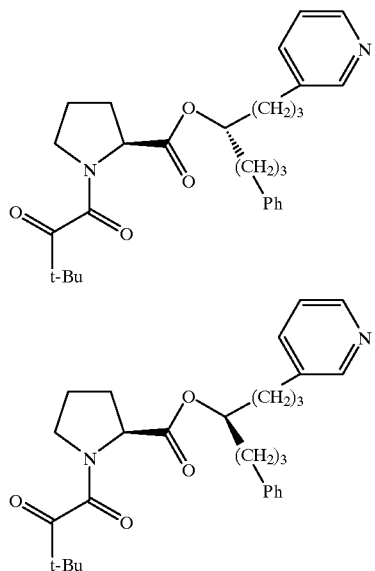

These compounds, which are named L-Proline, 1-(3,3-dimethyl-1,2-dioxobutyl)-,1-(3-phenylpropyl)-4-(3-pyridinyl) butyl ester, (S) and L-Proline, 1-(3,3-dimethyl-1,2-dioxobutyl)-1-(3-phenylpropyl)-4-(3-pyridinyl) butyl ester, (R), are disclosed in Armistead et al., Int. Appl. WO9407858 A1, which was published Apr. 14, 1994.

Example 50

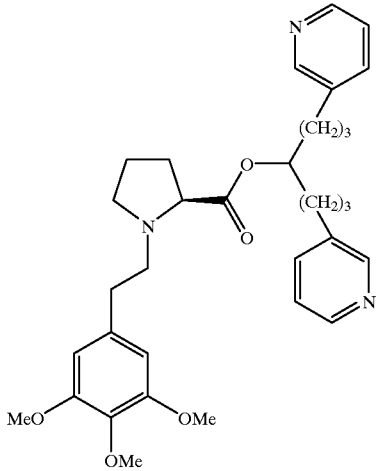

This compound, which is named L-Proline, 1-oxo(3,4,5-trimethoxyphenyl) acetyll-, 4-(3-pyridinyl)-1-[3-(3-pyridinyl) propyl] butyl ester, is disclosed in Armistead et al., Int. Appl. WO9407858 A1, which was published Apr. 14, 1994.

Example 51

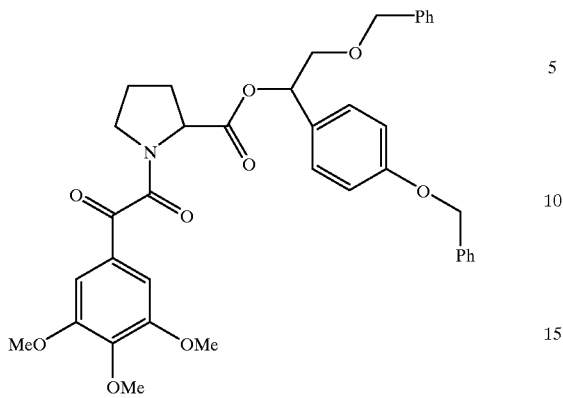

This compound, which is named L-Proline, 1-[oxo(3,4, 5-trimethoxyphenyl) acetyl]-, 2-(phenylmethoxy)-1-[(phenylmethoxy)phenyl]ethyl ester, is disclosed in Armistead et al., Int. Appl. WO9407858 A1, which was ublished Apr. 14, 1994.

Example 52

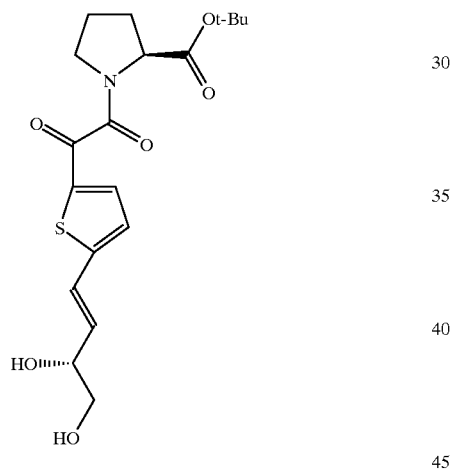

This compound, which is named L-Proline, 1-[[5-(3,4-dihydroxy-1-butenyl)-2-thienyl] oxoacetyl]-, 1,1-dimethylethyl ester, (R), is disclosed in Hauske et al., Bioorg. Med. Chem. Lett., 1994, 4(17), 2097–102.

Example 53

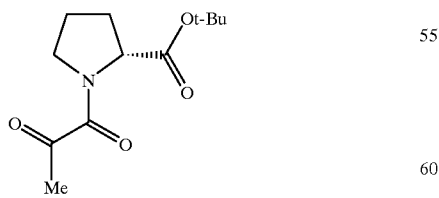

This compound, which is named L-Proline, 1-(1,2-dioxopropyl)-, 1,1-dimethylethyl ester, is disclosed in Ryan, J. and Chung, A., U.S. Pat. No. 4,766,110, which issued Aug. 23, 1988.

Example 54

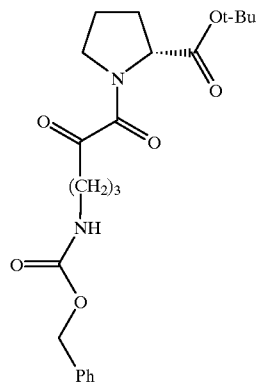

This compound, which is named L-Proline, 1-[1,2-dioxo-5-[[(phenylmethoxy)carbonyl]amino]pentyl]-, 1,1-diemthylethyl ester, is disclosed in Ryan, J. and Chung, A., U.S. Pat. No. 4,766,110, which issued Aug. 23, 1988.

Example 55

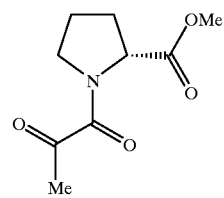

This compound, which is named L-Proline, 1-(1,2-dioxopropyl)-, methyl ester, is disclosed in Ryan, J. and Chung, A., U.S. Pat. No. 4,766,110, which issued Aug. 23, 1988.

Example 56

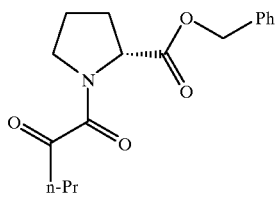

This compound, which is named L-Proline, 1-(1,2-dioxopentyl)-, phenylmethyl ester, is disclosed in Nestor, J., U.S. Pat. No. 4,762,821, which issued Aug. 9, 1988.

Example 57

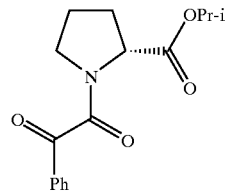

This compound, which is named L-Proline, 1-(oxophenylacetyl)-, 1-methylethyl ester, is disclosed in Soai, K. and Ishizaki, M., *Pept. Chem.*, 1987, Volume Date 1986, 24th, 327–30.

Example 58

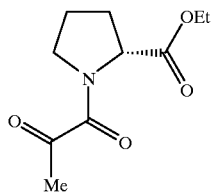

This compound, which is named L-Proline, 1-( 1,2-dioxopropyl)-, ethyl ester, is disclosed in Munegumi et al., *Bull. Chem. Soc. Jpn.*, 1987, 60(1), 249–53.

Example 59

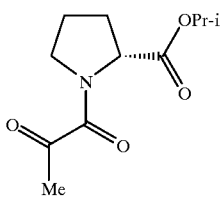

This compound, which is named L-Proline, 1-(1,2-dioxopropyl)-, 1-methylethyl ester, is disclosed in Munegumi et al., *Bull. Chem. Soc. Jpn.*, 1987, 60(1), 249–53.

Example 60

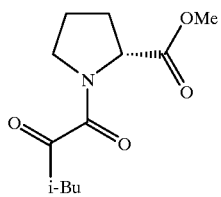

This compound, which is named L-Proline, 1-(4-methyl-1,2-dioxopentyl)-, methyl ester, is disclosed in Soai et ale, *Chem. Lett.*, 1986, (11), 1897–900.

Example 61

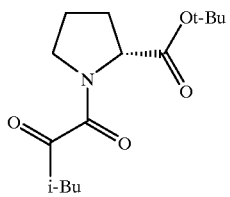

This compound, which is named L-Proline, 1-(4-methyl-1,2-dioxopentyl)-, 1,1-dimethylethyl ester, is disclosed in Soai et al., *Chem. Lett.*, 1986, (11), 1897–900.

Example 62

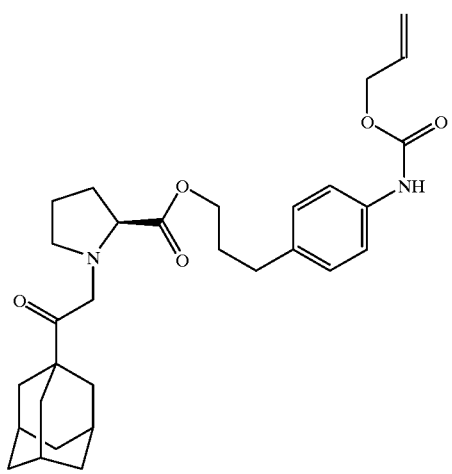

This compound, which is named L-Proline, 1-[2-adamantan-1-yl-2-oxoethyl] 3-(4-(N-carboallyloxy) aminopropyl ester hydrochloride, is disclosed in Connell et al., European Patent No. 0 564 924 A2, which was published Oct. 13, 1993.

Example 63

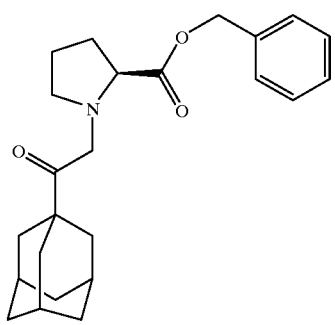

This compound, which is named L-Proline, 1-(2-adamantan-1-yl-2-oxoethyl)benzyl ester, is disclosed in Connell et al., European Patent No. 0 564 924 A2, which was published Oct. 13, 1993.

Example 64

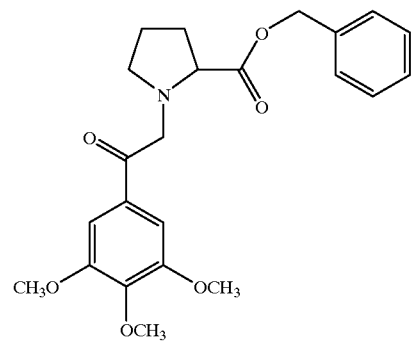

This compound, which is named L-Proline, 1-[2-(3,4,5-trimethoxyphenyl)-2-oxoethyl] benzyl ester hydrochloride, is disclosed in Connell et al., European Patent No. 0 564 924 A2, which was published Oct. 13, 1993.

Example 65

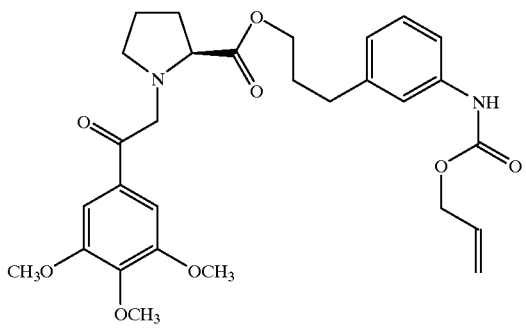

This compound, which is named L-Proline, 1-[2-(3,4,5-trimethoxyphenyl)-2-oxoethyl] 3-(4-[N-carboallyloxy] aminophenyl) propyl ester hydrochloride, is disclosed in Connell et al., European Patent No. 0 564 924 A2, which was published Oct. 13, 1993.

The inventive structure being thus described, it will be obvious that the same may be varied in many ways. Such variations are not to be regarded as a departure from the spirit and scope of the invention and all such modification are intended to be included within the scope of the following claims.

What is claimed is:

1. A method for treating a neurological disorder in an anaimal comprising administering to the animal a therapcutically effective amount of a N-linked 1,2-diketo prolyl ester compound or a N-linked 1,2-diketo prolyl amide compound, wherein said ester compound or said amide compound is non-immunosuppressive.

2. A method of promoting neuronal regeneration and growth in animals, comprising administering to a mammal an effective amount of a N-linked 1,2-diketo prolyl ester compound or a N-linked 1,2-diketo prolyl amide compound, wherein said ester compound or said amide compound is non-immunosuppressive.

3. A method of preventing neurodegeneration in an animal comprising administering to an animal an effective amount of a N-linked 1,2-diketo prolyl ester compound, or a N-linked 1,2-diketo prolyl amide compound, wherein said ester compound or said amide compound is non-immunosuppressive.

4. The non-immunosuppressive neurotrophic N-linked 1,2-diketo prolyl ester compound or the non-immunosuppressive neurotrophic N-linked 1,2-diketo prolyl amide compound of claim 1, wherein said ester compound and said amide compound have a molecular weight less than 800 Daltons.

* * * * *

UNITED STATES PATENT AND TRADEMARK OFFICE
CERTIFICATE OF CORRECTION

PATENT NO. : 6,291,510 B1  Page 1 of 1
DATED : September 18, 2001
INVENTOR(S) : Hamilton, Steiner It is certified that error appears in the above-identified patent and that said Letters Patent is hereby corrected as shown below:

Column 38, claim 2,
Line 10, after "growth in" and before ", comprising administering to a mammal", delete "animals" and insert thereof -- mammals --.

Column 38,
Lines 20-25, delete claim 4 in its entirety.

Signed and Sealed this

Ninth Day of April, 2002

Attest:

JAMES E. ROGAN
Attesting Officer  Director of the United States Patent and Trademark Office